US011304676B2

(12) United States Patent
Dayton et al.

(10) Patent No.: US 11,304,676 B2
(45) Date of Patent: Apr. 19, 2022

(54) APPARATUSES, SYSTEMS, AND METHODS FOR PRECLINICAL ULTRASOUND IMAGING OF SUBJECTS

(71) Applicants: The University of North Carolina at Chapel Hill, Chapel Hill, NC (US); SonoVol, Inc., Research Triangle Park, NC (US)

(72) Inventors: Paul Alexander Dayton, Carrboro, NC (US); Ryan Christopher Gessner, Durham, NC (US); James Owen Butler, Durham, NC (US); Max Stephan Harlacher, Chapel Hill, NC (US); Nicholas Allan Norman, Austin, TX (US)

(73) Assignees: THE UNIVERSITY OF NORTH CAROLINA AT CHAPEL HILL, Chapel Hill, NC (US); SONOVOL, INC., Research Triangle Park, NC (US)

( * ) Notice: Subject to any disclaimer, the term of this patent is extended or adjusted under 35 U.S.C. 154(b) by 321 days.

(21) Appl. No.: 15/545,947

(22) PCT Filed: Jan. 25, 2016

(86) PCT No.: PCT/US2016/014685
§ 371 (c)(1),
(2) Date: Jul. 24, 2017

(87) PCT Pub. No.: WO2016/118947
PCT Pub. Date: Jul. 28, 2016

(65) Prior Publication Data
US 2018/0000444 A1 Jan. 4, 2018

Related U.S. Application Data

(60) Provisional application No. 62/107,321, filed on Jan. 23, 2015.

(51) Int. Cl.
*A61B 8/08* (2006.01)
*A61B 8/00* (2006.01)
*A61B 6/00* (2006.01)

(52) U.S. Cl.
CPC ........... *A61B 8/08* (2013.01); *A61B 6/508* (2013.01); *A61B 8/0883* (2013.01);
(Continued)

(58) Field of Classification Search
CPC ....... A61B 8/08; A61B 8/0883; A61B 8/4218; A61B 8/4281; A61B 6/508; A61B 8/4416;
(Continued)

(56) References Cited

U.S. PATENT DOCUMENTS 4,282,880 A * 8/1981 Gardineer ............ A61B 8/0825
128/915
4,597,005 A * 6/1986 Baleshta ............. H04N 11/042
348/463
(Continued)

FOREIGN PATENT DOCUMENTS

CA 2 846 315 A1 9/2014
CN 103156637 A 6/2013
(Continued)

OTHER PUBLICATIONS

Garson ["3D Cardiac Motion Estimation using RF Signal Decorrelation", 2008 IEEE International Ultrasonics Symposium Proceedings] (Year: 2008).*
(Continued)

*Primary Examiner* — Oommen Jacob
(74) *Attorney, Agent, or Firm* — Jenkins, Wilson, Taylor & Hunt, P.A.

(57) ABSTRACT

Apparatuses, systems, and methods for preclinical ultrasound imaging of subjects are provided. In one aspect, the
(Continued)

apparatus can include a platform on which a subject is positionable and at least one motion stage for controlling a spatial position of at least one ultrasound transducer relative to the platform in order to acquire ultrasound image data of the subject. Methods for preclinical ultrasound raster scanning of at least one organ or tissue in a subject are also provided, where the at least one organ or tissue is a heart.

32 Claims, 22 Drawing Sheets

(52) U.S. Cl.
CPC .......... *A61B 8/4218* (2013.01); *A61B 8/4281* (2013.01); *A61B 8/4416* (2013.01); *A61B 6/4417* (2013.01); *A61B 8/52* (2013.01)

(58) Field of Classification Search
CPC .................. A61B 8/52; A61B 6/4417; A61B 8/4209–4218; A61B 6/50; A61B 6/502
USPC .................................................. 600/437, 407
See application file for complete search history.

(56) References Cited

U.S. PATENT DOCUMENTS

| | | | |
|---|---|---|---|
| 4,816,567 A | 3/1989 | Cabilly et al. | |
| 5,070,879 A | 12/1991 | Herres | |
| 5,088,499 A | 2/1992 | Unger | |
| 5,147,631 A | 9/1992 | Glajch et al. | |
| 5,178,150 A * | 1/1993 | Silverstein | A61B 1/018 600/446 |
| 5,655,535 A | 8/1997 | Friemel et al. | |
| 5,670,719 A | 9/1997 | Madsen et al. | |
| 5,779,641 A | 7/1998 | Hatfield et al. | |
| 5,831,166 A * | 11/1998 | Kozuka | B01D 21/283 73/570 |
| 5,846,204 A | 12/1998 | Solomon | |
| 5,872,571 A | 2/1999 | Arling | |
| 5,899,861 A | 5/1999 | Friemel et al. | |
| 6,106,470 A | 8/2000 | Geiser et al. | |
| 6,108,572 A | 8/2000 | Panda et al. | |
| 6,117,078 A | 9/2000 | Lysyansky et al. | |
| 6,172,197 B1 | 1/2001 | McCafferty et al. | |
| 6,221,018 B1 | 4/2001 | Ramamurthy et al. | |
| 6,231,834 B1 | 5/2001 | Unger et al. | |
| 6,245,318 B1 | 6/2001 | Klibanov et al. | |
| 6,248,516 B1 | 6/2001 | Winter et al. | |
| 6,254,538 B1 * | 7/2001 | Downey | A61B 8/0825 128/915 |
| 6,254,852 B1 | 7/2001 | Glajch et al. | |
| 6,291,158 B1 | 9/2001 | Winter et al. | |
| 6,318,179 B1 | 11/2001 | Hamilton et al. | |
| 6,417,857 B2 * | 7/2002 | Finger | G01S 7/52023 345/505 |
| 6,425,865 B1 * | 7/2002 | Salcudean | A61B 8/0875 600/111 |
| 6,468,265 B1 * | 10/2002 | Evans | A61B 34/32 600/103 |
| 6,574,499 B1 * | 6/2003 | Dines | A61B 6/0414 128/915 |
| 6,607,488 B1 | 8/2003 | Jackson et al. | |
| 6,733,458 B1 | 5/2004 | Steins et al. | |
| 6,748,259 B1 * | 6/2004 | Benaron | A61B 5/0071 250/339.02 |
| 6,782,752 B2 * | 8/2004 | Basir | G01N 29/024 73/600 |
| 7,051,654 B2 | 5/2006 | Boland et al. | |
| 7,155,274 B1 * | 12/2006 | Wake | A61B 5/0062 600/476 |
| 7,556,602 B2 * | 7/2009 | Wang | A61B 6/463 600/437 |
| 7,597,664 B2 | 10/2009 | Jones et al. | |
| 7,603,966 B1 * | 10/2009 | Beebe | A61D 3/00 119/755 |
| 7,740,584 B2 | 6/2010 | Donaldson et al. | |
| 7,862,509 B2 | 1/2011 | Jones et al. | |
| 8,090,164 B2 | 1/2012 | Bullitt et al. | |
| 8,102,392 B2 | 1/2012 | Yamagata et al. | |
| 8,226,560 B2 | 7/2012 | Arai et al. | |
| 8,233,681 B2 | 7/2012 | Aylward et al. | |
| 8,660,631 B2 * | 2/2014 | Feke | A61B 6/00 600/407 |
| 8,717,843 B2 | 6/2014 | Cerofolini | |
| 9,340,581 B2 | 5/2016 | Hallahan et al. | |
| 9,375,397 B2 | 6/2016 | Bettinger et al. | |
| 9,427,410 B2 | 8/2016 | Dayton et al. | |
| 9,532,769 B2 | 1/2017 | Dayton et al. | |
| 10,653,321 B2 * | 5/2020 | Wang | A61B 8/4245 |
| 2001/0005776 A1 | 6/2001 | Holley et al. | |
| 2002/0099290 A1 | 7/2002 | Haddad | |
| 2002/0143252 A1 * | 10/2002 | Dunne | G10K 11/004 600/437 |
| 2002/0156375 A1 | 10/2002 | Kessman et al. | |
| 2003/0065265 A1 | 4/2003 | Jackson et al. | |
| 2003/0078490 A1 * | 4/2003 | Damasco | A61B 18/02 600/407 |
| 2003/0167004 A1 * | 9/2003 | Dines | A61B 6/4417 600/437 |
| 2004/0010192 A1 * | 1/2004 | Benaron | B82Y 10/00 600/431 |
| 2004/0236219 A1 * | 11/2004 | Liu | G01S 7/52079 600/437 |
| 2005/0090740 A1 | 4/2005 | Raitzer et al. | |
| 2005/0119570 A1 | 6/2005 | Lewis et al. | |
| 2006/0004291 A1 | 1/2006 | Heimdal et al. | |
| 2006/0069536 A1 | 3/2006 | Butsev et al. | |
| 2006/0074287 A1 * | 4/2006 | Neumann | A61B 6/548 600/407 |
| 2006/0116576 A1 | 6/2006 | McGee et al. | |
| 2006/0241432 A1 | 10/2006 | Herline et al. | |
| 2007/0016035 A1 | 1/2007 | Hashimoto | |
| 2007/0112272 A1 | 5/2007 | Park et al. | |
| 2007/0167787 A1 | 7/2007 | Glossop et al. | |
| 2007/0274585 A1 * | 11/2007 | Zhang | G06F 19/321 382/132 |
| 2008/0045865 A1 | 2/2008 | Kislev | |
| 2008/0146932 A1 | 6/2008 | Chalana et al. | |
| 2008/0146933 A1 | 6/2008 | Lewis et al. | |
| 2008/0208044 A1 | 8/2008 | Lecoq et al. | |
| 2008/0262356 A1 | 10/2008 | Chalana et al. | |
| 2009/0005711 A1 * | 1/2009 | Konofagou | A61B 8/0816 601/2 |
| 2009/0054779 A1 | 2/2009 | Chomas et al. | |
| 2009/0062651 A1 | 3/2009 | Chomas et al. | |
| 2009/0221908 A1 | 9/2009 | Glossop | |
| 2010/0036242 A1 | 2/2010 | Yuk et al. | |
| 2010/0056914 A1 * | 3/2010 | Bruggers | A61B 5/0035 600/439 |
| 2010/0074845 A1 * | 3/2010 | Gambhir | A61K 49/225 424/9.1 |
| 2010/0125192 A1 * | 5/2010 | Chopra | A61N 7/02 600/411 |
| 2010/0224782 A1 | 9/2010 | Pan et al. | |
| 2010/0262013 A1 | 10/2010 | Smith et al. | |
| 2010/0268503 A1 | 10/2010 | Specht et al. | |
| 2011/0218438 A1 | 9/2011 | Hsieh et al. | |
| 2011/0237945 A1 | 9/2011 | Foroughi et al. | |
| 2011/0250688 A1 | 10/2011 | Hasan | |
| 2011/0306885 A1 | 12/2011 | Specht | |
| 2012/0035742 A1 | 2/2012 | Vunjak-Novakovic et al. | |
| 2012/0116226 A1 | 5/2012 | Specht | |
| 2012/0220869 A1 | 8/2012 | Dayton et al. | |
| 2012/0321033 A1 * | 12/2012 | Stearns | A61B 6/0487 378/4 |
| 2012/0323112 A1 * | 12/2012 | Jokerst | A61B 8/481 600/420 |
| 2012/0323124 A1 | 12/2012 | Corbett, III et al. | |
| 2013/0006114 A1 | 1/2013 | Pellegretti | |
| 2013/0177972 A1 | 7/2013 | Green et al. | |

(56) References Cited

U.S. PATENT DOCUMENTS

| | | | |
|---|---|---|---|
| 2013/0338474 | A9* | 12/2013 | Carson ............... G01N 29/2418 600/407 |
| 2015/0037808 | A1 | 2/2015 | Donaty |
| 2016/0216199 | A1 | 7/2016 | Hofmeister et al. |
| 2016/0262628 | A1* | 9/2016 | Wang .................. A61B 5/0095 |
| 2017/0050076 | A1 | 2/2017 | Beals |
| 2017/0198252 | A1 | 7/2017 | Mironov et al. |
| 2017/0276649 | A1 | 9/2017 | Schmitz et al. |
| 2018/0000444 | A1* | 1/2018 | Dayton ............... A61B 8/4281 |
| 2018/0306685 | A1 | 10/2018 | Boguslavsky et al. |
| 2019/0242896 | A1 | 8/2019 | Gessner et al. |

FOREIGN PATENT DOCUMENTS

| | | |
|---|---|---|
| EP | 0 514 584 A2 | 11/1992 |
| EP | 1 013 226 A2 | 6/2000 |
| EP | 1 046 929 B1 | 10/2000 |
| EP | 0 813 074 B1 | 9/2001 |
| EP | 1 167 996 B1 | 11/2012 |
| EP | 2 666 430 A1 | 11/2013 |
| EP | 2 666 431 A1 | 11/2013 |
| EP | 2 666 433 A1 | 11/2013 |
| EP | 2 666 432 B1 | 3/2015 |
| EP | 3 247 281 B1 | 12/2020 |
| JP | 4099340 B2 | 6/2008 |
| JP | 2010-115483 A | 5/2010 |
| JP | 5192508 B2 | 5/2013 |
| WO | WO 92/22653 | 12/1992 |
| WO | WO 2001/001845 A2 | 1/2001 |
| WO | WO 2005/023086 A2 | 3/2005 |
| WO | WO 2006/031526 A2 | 3/2006 |
| WO | WO 2009/026644 A1 | 3/2009 |
| WO | WO 2012/024201 A1 | 2/2012 |
| WO | WO 2013/170053 A1 | 11/2013 |
| WO | WO 2017/214637 A1 | 12/2017 |
| WO | WO 2018/045373 A1 | 3/2018 |

OTHER PUBLICATIONS

Communication of the Extended European Search Report for European Patent Application Serial No. 16740894.7 (dated Sep. 5, 2018).
Notification of Transmittal of the International Search Report and the Written Opinion of the International Searching Authority, or the Declaration for International Application No. PCT/US2016/014685 (dated Jun. 30, 2016).
ORCA Bioreactor Operator's Manual, Harvard Apparatus Regenerative Technology, Revision 1.0, pp. 1-56 (Jan. 22, 2013).
Notification of Transmittal of the International Search Report and the Written Opinion of the International Searching Authority, or the Declaration for International Application No. PCT/US17/50076 (dated Jan. 12, 2018).
Communication of European publication number and information on the application of Article 67(3) EPC for European Patent Application No. 16740894.7 (dated Nov. 3, 2017).
Nagao et al., "Ultrasound-Guided Photoacoustic Imaging-Directed Re-Endothelialization of Acellular Vasculature Leads to Improved Vascular Performance," Acta Biomater, vol. 32, pp. 35-45 (2016).
Shelton et al., "Molecular Acoustic Angiography: A New Technique for High Resolution Superharmonic Ultrasound Molecular Imaging," Ultrasound in Medicine & Biology, vol. 42, No. 3, pp. 1-26 (2016).
Collins et al., "United States Renal Data System Public Health Surveillance of Chronic Kidney Disease and End-Stage Renal Disease," Kidney International Supplements, vol. 5, pp. 2-7 (2015).
Keravnou et al., "Image-Guided Sonoporation in an Ex Vivo Machine Perfused Porcine Liver," J Ther Ultrasound, vol. 3, pp. 1-2 (2015).
Ko et al., "Bioengineered Transplantable Porcine Livers with Re-Endothelialized Vasculature," Biomaterials, vol. 40, pp. 72-79 (2015).
Northup et al., "Excess Mortality on the Liver Transplant Waiting List: Unintended Policy Consquences and Model for End-Stage Liver Disease (MELD) Inflation," Hepatology, vol. 61, No. 1, pp. 285-291 (2015).
Azene et al., "Tracking of Stem Cells In Vivo for Cardiovascular Applications," J Cardiovasc Magn Reson, vol. 16, No. 1, pp. 1-22 (2014).
Go et al., "Heart Disease and Stroke Statistics—2014 Update," Circulation, vol. 129, No. 3, pp. 1-536 (2014).
Dutta et al., "Non-Invasive Assessment of Elastic Modulus of Arterial Constructs During Cell Culture Using Ultrasound Elasticity Imaging," Ultrasound Med Biol, vol. 39, No. 11, pp. 1-23 (2013).
Gessner et al., "Functional Ultrasound Imaging for Assessment of Extracellular Matrix Scaffolds Used for Liver Organoid Formation," Biomaterials, vol. 34, pp. 1-24 (2013).
Streeter et al., "A Comparative Evaluation of Ultrasound Molecular Imaging, Perfusion Imaging, and Volume Measurements in Evaluating Response to Therapy in Patient-Derived Xenografts," Technol Cancer Res Treat., vol. 12, No. 4, pp. 1-20 (2013).
Yu et al., "Non-Invasive Characterization of Polyurethane-Based Tissue Constructs in a Rat Abdominal Repair Model Using High Frequency Ultrasound Elasticity Imaging," Biomaterials, vol. 34, No. 11, pp. 1-18 (2013).
Collins et al., "United States Renal Data System 2011 Annual Data Report: Atlas of Chronic Kidney Disease & End-Stage Renal Disease in the United States," American Journal of Kidney Diseases: The Official Journal of the National Kidney Foundation, vol. 59, pp. evii (2012).
Gessner et al., "An In Vivo Validation of the Application of Acoustic Radiation Force to Enhance the Diagnostic Utility of Molecular Imaging Using 3D Ultrasound," Ultrasound Med Biol., vol. 38, No. 4, pp. 1-18 (2012).
Gessner et al., "Mapping Microvasculature with Acoustic Angiography Yields Quantifiable Differences Between Healthy and Tumor-Bearing Tissue Volumes in a Rodent Model," Radiology, vol. 264, No. 3, pp. 733-740 (2012).
Pauwels et al., "Global Strategy for the Diagnosis, Management, and Prevention of Chronic Obstructive Pulmonary Disease," American Journal of Respiratory and Critical Care Medicine, vol. 163, pp. 1256-1276 (2001).
Popp et al., "An Instrumented Bioreactor for Mechanical Stimulation and Real-Time, Nondestructive Evaluation of Engineered Cartilage Tissue," Journal of Medical Devices, vol. 6, pp. 1-7 (Jun. 2012).
Puppi et al., "Improving the Techniques for Human Hepatocyte Transplantation," Report from a Consensus Meeting in London/Cell Transplantation, vol. 21, Issue 1, pp. 1-24 (2012).
Smith et al., "Kidney, Pancreas and Liver Allocation and Distribution in the United States," Am J of Transplant, vol. 12, pp. 1-36 (2012).
Badylak et al., "Whole-Organ Tissue Engineering: Decellularization and Recellularization of Three-Dimensional Matrix Scaffolds," Annu. Rev. Biomed. Eng., vol. 13, pp. 27-53 (2011).
Baptista et al., "The Use of Whole Organ Decellularization for the Generation of a Vascularized Liver Organoid," Hepatology, vol. 53, No. 2, pp. 604-617 (2011).
Gessner et al., "3D Microvessel-Mimicking Ultrasound Phantoms Produced with a Scanning Motion System," Ultrasound Med Biol., vol. 37, No. 5, pp. 1-12 (2011).
Kogan et al., "Validation of Dynamic Contrast-Enhanced Ultrasound in Rodent Kidneys as an Absolute Quantitative Method for Measuring Blood Perfusion," Ultra Med Biol., vol. 37, pp. 900-908 (2011).
Kooiman et al., "Sonoporation of endothelial cells by vibrating targeted microbubbles," J. Control Release, vol. 154, pp. 35-41 (2011).
Lalande et al., "Magnetic Resonance Imaging Tracking of Human Adipose Derived Stromal Cells Within Three-Dimensional Scaffolds for Bone Tissue Engineering," Eur Cell Mater, vol. 21, pp. 341-354 (2011).
Streeter et al., "Assessment of Molecular Imaging of Angiogenesis with Three-Dimensional Ultrasonography," Mol Imaging, vol. 10, No. 6, pp. 1-18 (2011).
Uygun et al., "Decellularization and Recellularization of Whole Livers," Journal of Visualized Experiments, vol. 48, pp. 1-4 (2011).

(56) References Cited

OTHER PUBLICATIONS

Wang et al., "Lineage Restriction of Human Hepatic Stem Cells to Mature Fates Is Made Efficient by Tissue-Specific Biomatrix Scaffolds," Hepatology, vol. 53, pp. 293-305 (2011).
Anderson et al., "scVEGF Microbubble Ultrasound Contrast Agents: A Novel Probe for Ultrasound Molecular Imaging of Tumor Angiogenesis," Invest Radiol, vol. 45, pp. 1-17 (2010).
Feingold et al., "Quantitative Volumetric Perfusion Mapping of the Microvasculature Using Contrast Ultrasound," Invest Radiol., vol. 45, No. 10, pp. 1-14 (2010).
Gessner et al., "High-Resolution, High-Contrast Ultrasound Imaging Using a Prototype Dual-Frequency Transducer: In Vitro and In Viro Studies," IEEE Transactions on Ultrasonics, Ferroelectrics, and Frequency Control, vol. 57, No. 8, pp. 1772-1781 (2010).
Logeart-Avramoglou et al., "In Vitro and In Vivo Bioluminescent Quantification of Viable Stem Cells in Engineered Constructs," Tissue Eng Part C Methods, vol. 16, No. 3, pp. 447-458 (2010).
Smith et al., "A Comparison of Imaging Methodologies for 3D Tissue Engineering," Microscopy Research and Technique, vol. 73, pp. 1123-1133 (2010).
Uygun et al., "Organ Reengineering Through Development of a Transplantable Recellularized Liver Graft Using Decellularized Liver Matrix," Nature Medicine, vol. 16, pp. 814-820 (2010).
Baptista et al., "Whole Organ Decellularization—A Tool for Bioscaffold Fabrication and Organ Bioengineering," IEEE Eng Med Biol Soc., pp. 6526-6529 (2009).
Behler et al., "ARFI Imaging for Noninvasive Material Characterization of Atherosclerosis Part II: Toward In Vivo Characterization," Ultrasound Med Biol., vol. 35, No. 2, pp. 1-30 (2009).
Catapano et al., "Transport Advances in Disposable Bioreactors for Liver Tissue Engineering," Adv Biochem Engin/Biotechnol., vol. 115, pp. 117-143 (2009).
Kuliszewski et al., "Molecular Imaging of Endothelial Progenitor Cell Engraftment Using Contrast-Enhanced Ultrasound and Targeted Microbubbles," Cardiovasc Res., vol. 83, No. 4, pp. 653-662 (2009).
Liang et al., "Imaging Engineered Tissues Using Structural and Functional Optical Coherence Tomography," Journal of Biophotonics, vol. 2, No. 11, pp. 643-655 (2009).
Terrovitis et al., "Noninvasive Quantification and Optimization of Acute Cell Retention by In Vivo Positron Emission Tomography After Intramyocardial Cardiac-Derived Stem Cell Delivery," J Am Coll Cardiol, vol. 54, No. 17, pp. 1-17 (2009).
Gerlach et al., "Bioartificial Liver Systems: Why, What, Whither?" Regan Med., vol. 3, No. 4, pp. 575-595 (2008).
Hwang et al., "Real-Time In Vivo Monitoring of Viable Stem Cells Implanted on Biocompatible Scaffolds," Eur J Nucl Med Imaging, vol. 35, No. 10, pp. 1887-1898 (2008).
Kim et al., "Non-Invasive Monitoring of Tissue Scaffold Degradation Using Ultrasound Elasticity Imaging," Acta Biomater, vol. 4, No. 4, pp. 1-17 (2008).
Xu et al., "Monitoring Tissue Engineering Using Magnetic Resonance Imaging," Biological Systems Engineering, vol. 106, pp. 515-527 (2008).
Young et al., "Microcomputed Tomography Characterization of Neovascularization in Bone Tissue Engineering Applications," Tissue Engineering: Part B, vol. 14, No. 3, pp. 295-306 (2008).
Kaufmann et al., "Molecular Imaging of Inflammation in Atherosclerosis with Targeting Ultrasound of Vascular Cell Adhesion Molecule-1," vol. 116, No. 3, pp. 276-284 (2007).
De Boer, et al., "Bioluminescent Imaging: Emerging Technology for Non-Invasive Imaging of Bone Tissue Engineering," Biomaterials, vol. 27, No. 9, pp. 1851-1858 (2006).
McGuigan et al., "Vascularized Organoid Engineered by Modular Assembly Enables Blood Perfusion," PNAS, vol. 103, No. 31, pp. 11461-11466 (2006).
Klibanov, "Ligand-Carrying Gas-Filled Microbubbles: Ultrasound Contrast Agents for Targeted Molecular Imaging," Bioconjug Chem, vol. 16, No. 1, pp. 9-17 (2005).
Kruse et al., "A New Imaging Strategy Using Wideband Transient Response of Ultrasound Contrast Agents," IEEE Transactions on Ultrasonics, Ferroelectrics, and Frequency Control, vol. 52, No. 8, pp. 1320-1409 (2005).
Mason et al., "Doppler Optical Coherence Tomography for Measuring Flow in Engineered Tissue," Biosens Bioelectron, vol. 20, No. 3, pp. 414-423 (2004).
Mason et al., "The Potential of Optical Coherence Tomography in the Engineering of Living Tissue," Phys Med Biol, vol. 49, No. 7, pp. 1097-1115 (2004).
Badylak, "The Extracellular Matrix as a Scaffold for Tissue Reconstruction," Cell & Developmental Biology, vol. 13, pp. 377-383 (2002).
Foster et al., "A New Ultrasound Instrument for In Vivo Microimaging of Mice," Ultrasound in Med. & Biol., vol. 28, No. 9, pp. 1165-1172 (2002).
Lindner et al., "Microvascular Rheology of Definity Microbubbles after Intra-Arterial and Intravenous Administration," J Am Soc of Echocardiogr., vol. 15, pp. 396-403 (2002).
Malhi et al., "Early Cell Transplantation in LEC Rats Modeling Wilson's Disease Eliminates Hepatic Copper with Reversal of Liver Disease," Gastroenterology, vol. 122, pp. 438-447 (2002).
Badylak et al., "Naturally Occurring Extracellular Matrix as a Scaffold for Musculoskeletal Repair," Clin Orthop Relat Res., pp. S333-S343 (1999).
Gupta et al., "Entry and Integration of Transplanted Hepatocytes in Rat Liver Plates Occur by Disruption of Hepatic Sinusoidal Endothelium," Hepatology, vol. 29, pp. 509-519 (1999).
Taylor et al., "Regenerating Functional Myocardium: Improved Performance After Skeletal Myoblast Transplantation," Nat Med., vol. 4, pp. 929-933 (1998).
Wei et al., "Quantification of Myocardial Blood Flow with Ultrasound-Induced Destruction of Microbubbles Administered as a Constant Venous Infusion," Circulation, vol. 97, pp. 473-483 (1998).
Reid et al., "Extracellular Matrix Gradients in the Space of Disse: Relevance to Liver Biology," Hepatology, vol. 15, pp. 1198-1203 (1992).
Darlington et al., "Growth and Hepatospecific Gene Expression of Human Hepatoma Cells in a Defined Medium," In Vitro Cell Dev Biol., vol. 23, pp. 349-354 (1987).
Knowles et al., "Human Hepatocellular Carcinoma Cell Lines Secrete the Major Plasma Proteins and Hepatitis B Surface Antigen," Science, vol. 209, pp. 497-499 (1980).
Communication under Rule 71(3) EPC Invention to Grant for European Patent Application Serial No. 16 740 894.7 (dated Jan. 31, 2020).
"Care and Maintenance of the 700-Series RMVTM Scanheads for Use with Vevo 770TM," VisualSonics, pp. 1-11 (Dec. 2004).
Communication under Rule 71(3) EPC for European Patent Application Serial No. 16 740 894.7 (dated Aug. 11, 2020).
Commonly-Assigned, co-pending U.S. Appl. No. 16/521,183 for "Methods, Systems, and Computer Readable Media for Translating Sample Plate Over Fixed Ultrasound Transducer," (Unpublished, filed Jul. 24, 2019).
"Vevo 770 High-Resolution Imaging System Operator Manual," VisualSonics, pp. 1-310 (2006).
Decision to grant a European patent pursuant to Article 97(1) EPC for European Patent Application Serial No. 16740894.7 (dated Nov. 5, 2020).
Kasoji et al., "Cavitation Enhancing Nanodroplets Mediate Efficient DNA Fragmentation in a Bench Top Ultrasonic Water Bath," PLoS ONE, vol. 10, No. 7, pp. 1-9 (2015).
Non-Final Office Action for U.S. Appl. No. 16/521,183 (dated Nov. 26, 2021).
Office Action for Canadian Patent Application Serial No. 2,974,377 (dated Nov. 15, 2021).

* cited by examiner

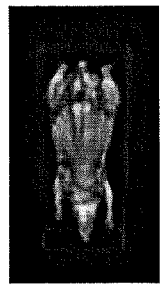
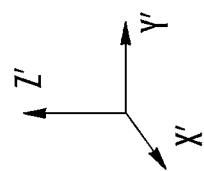
FIG. 13C
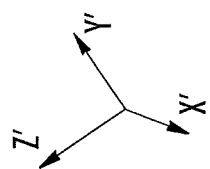
FIG. 13B
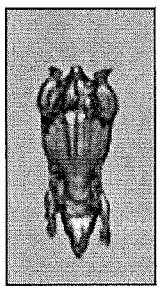
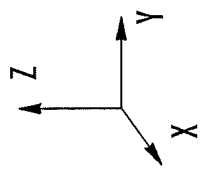
FIG. 13A

FIG. 18A
FIG. 18B

APPARATUSES, SYSTEMS, AND METHODS FOR PRECLINICAL ULTRASOUND IMAGING OF SUBJECTS

PRIORITY

This application claims the priority benefit of U.S. Provisional Patent Application Ser. No. 62/107,321, filed Jan. 23, 2015, which is incorporated by reference herein in its entirety.

GRANT INFORMATION

This invention was made with government support under Grant Nos. CA170665 and CA192482 awarded by the National Institutes of Health and Grant Nos. IIP-1346336 and IIP-1533978 awarded by the National Science Foundation. The government has certain rights in the invention.

TECHNICAL FIELD

The subject matter described herein relates to apparatuses, systems, and methods for use in ultrasound imaging. More particularly, the subject matter described herein relates to apparatuses, systems, and methods for preclinical ultrasound imaging of subjects.

BACKGROUND

Preclinical drug development researchers in both industry and academia rely on a variety of imaging techniques to visualize the effects caused by their novel therapeutic candidates within rodent disease models. "Molecular" or "functional" imaging techniques allow researchers to visualize processes occurring at the cellular level, which are indicative of a presence of disease. These imaging strategies—such as optical, Single Photon Emission Computed Tomography (SPECT), and Positron Emission Tomography (PET)—are extremely sensitive to contrast agents designed to target various disease processes of interest, though are not well suited to visualize anatomical features, such as tumor boundaries. Conversely, anatomical imaging strategies—such as magnetic resonance imaging (MRI), computed tomography (CT), and ultrasound—enable researchers to visualize the physical boundaries of anatomical structures, as well as the relative locations and morphologies of disease sites and healthy anatomy. These anatomical imaging approaches are less proficient, however, at detecting any processes not occurring at a gross phenotypic scale. Combining these two complimentary strategies is an intuitive approach to maximizing sensitivity for disease detection or for monitoring therapeutic response, and is widely implemented in both clinical and preclinical settings worldwide in the form of SPECT-CT and PET-CT systems.

Though not widely produced, a combination of MRI and PET (MR-PET) systems has recently been developed and offer a lower radiation-dose alternative to the CT approaches (albeit in exchange for an increase in financial and time expenses). Of the anatomical imaging approaches, ultrasound is often the most attractive because of the following: (a) it is innocuous for both user and patient, (b) it is the most portable of any of the modalities, (c) it is real-time, and (d) significantly the least expensive. Despite these attractive advantages, products to enable ultrasound-based multimodality clinical and preclinical imaging are scarce.

Accordingly, an efficient, flexible, and customizable platform that enables researchers to acquire whole-body anatomical images of their preclinical animal models using either primary or after-market ultrasound systems and probes which may already be in use, and if necessary, allowing for immediate registration of their anatomical ultrasound data with the functional imaging acquisition method of their choice: PET, SPECT, or optical is needed.

SUMMARY

Apparatuses, systems, and methods for preclinical ultrasound imaging of subjects are provided herein. In some aspects, an apparatus for preclinical ultrasound imaging of a subject may comprise a platform on which a subject (e.g., a rodent) is positionable, and at least one motion stage for controlling a spatial position of at least one ultrasound transducer relative to the platform in order to acquire ultrasound image data of the subject.

In some aspects, a system for preclinical ultrasound imaging of a subject may comprise at least one ultrasound imaging system, at least one ultrasound transducer associated with the ultrasound imaging system and positionable relative to a subject (e.g., a rodent), and an apparatus. In some aspects, the apparatus may a platform on which the subject is positionable, and at least one motion stage for controlling a spatial position of at least one ultrasound transducer relative to the platform in order to acquire ultrasound image data of the subject.

In some aspects, a method for preclinical ultrasound imaging of a subject may comprise movably positioning a platform, on which a subject (e.g., a rodent) is positionable, controlling, by at least one motion stage, a spatial position of at least one ultrasound transducer relative to the platform, and acquiring ultrasound image data of the subject.

In some aspects, the present subject matter may provide a system and method for preclinical ultrasound raster scanning of at least one organ or tissue in a subject. The system may comprise at least one ultrasound imaging system, at least one ultrasound transducer associated with the at least one ultrasound imaging system and positionable relative to a subject, an apparatus comprising a platform on which the subject is positionable, and at least one motion stage for controlling a spatial position of the at least one ultrasound transducer relative to the platform in order to acquire ultrasound image data of the subject, and a computing platform having a hardware processor and a memory and being associated with the at least one ultrasound imaging system and the apparatus, wherein the computing platform is configured to collect one-dimensional (1D) ultrasound scan lines through translation of the at least one ultrasound transducer through a raster scan grid aligned over an approximation of a location of at least one organ or tissue in the subject, and to analyze the 1D ultrasound scan lines to build a two-dimensional (2D) or three-dimensional (3D) mesh of relevant surfaces of the at least one organ or tissue.

The method may comprise positioning a subject on a platform, controlling a spatial position of at least one ultrasound transducer relative to the platform in order to acquire ultrasound image data of the subject, collecting one-dimensional (1D) ultrasound lines by translating the at least one ultrasound transducer through a raster scan grid aligned over an approximation of a location of at least one organ or tissue in the subject, and analyzing the 1D ultrasound lines to build a two-dimensional (2D) or three-dimensional (3D) mesh of relevant surfaces of the at least one organ or tissue.

BRIEF DESCRIPTION OF THE DRAWINGS

Preferred embodiments of the subject matter described herein will now be explained with reference to the accompanying drawings, wherein like reference numerals represent like parts, of which:

FIGS. 13A-13C are screenshots illustrating an exemplary workflow for spatial mapping of a subject system for preclinical ultrasound imaging of a subject according to the subject matter disclosed herein;

FIG. 18A is a screenshot illustrating a single 2D ultrasound image of a subject;

FIG. 18B is a screenshot illustrating a three-angled composite 2D ultrasound image of a subject for preclinical ultrasound imaging of a subject according to the subject matter disclosed herein, where a field of view in FIG. 18A is smaller than a field of view in FIG. 18B;

DETAILED DESCRIPTION

Figure 1A:
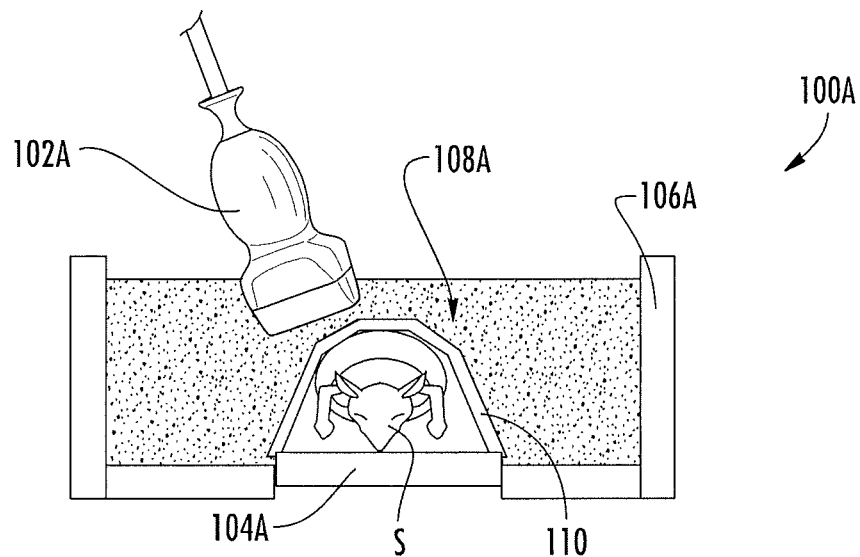
FIG. 1A is a front view illustrating an exemplary embodiment of an apparatus including a rigid reservoir for preclinical ultrasound imaging of a subject, wherein an imaging transducer scans substantially above the subject, according to the subject matter disclosed herein.

In accordance with the subject matter herein apparatuses, systems, and related methods for preclinical ultrasound imaging of subjects, as well as a method for raster scanning a subject, are disclosed. The apparatuses, systems, and related methods for preclinical ultrasound imaging of subjects may provide an efficient, flexible, and customizable platform that enables researchers to acquire whole-body anatomical images of preclinical animal models using any ultrasound systems and/or probes, while allowing for immediate registration of anatomical ultrasound data with functional imaging acquisition method of their choice: Positron Emission Tomography (PET), Single Photon Emission Computed Tomography (SPECT), optical, cryoimaging, etc.

Small animal models, specifically rodents, serve as models for human disease across a broad spectrum of pathologies. Animal models offer scientists a way to uncover underlying mechanisms for disease process, as well as study drug efficacy and toxicity profiles in living organisms. Until the advent of non-invasive imaging, large numbers of animals expressing a given disease phenotype were required for preclinical studies, as the only method to assess disease presence or response to a candidate therapeutic was through terminal strategies (necropsy, histology, etc.). By comparison, non-invasive imaging methods enable researchers to interrogate the structure and function of bodily tissues without the need to sacrifice for each assessment time-point, and thus drastically reduce number of animals needed for preclinical studies.

There are two principal types of imaging modalities: structural (i.e., anatomical) and functional. Structural imaging modalities allow for the visualization and assessment of physical properties (i.e., morphology, shape, size, texture, density, etc.) of tissue. Functional imaging modalities allow for the visualization and assessment of sub-resolution biological processes (i.e., inflammation, angiogenesis, metabolic demand, etc.) through the implementation of a contrast agent or reporter compound. Magnetic Resonance Imaging (MRI), Computed Tomography (CT), and Ultrasound (US) are examples of imaging modalities that are primarily used for anatomical imaging purposes. In vivo optical (bioluminescence and fluorescence) imaging, cryoimaging, SPECT, and PET are examples of functional imaging modalities.

Ultrasound offers several advantages over the other anatomical imaging modalities: it acquires real-time images, is non-invasive, is relatively portable, and is inexpensive. Accordingly, the apparatuses, systems, and methods described herein offer a novel approach to anatomical imaging of small animals using ultrasound (synonymous with "preclinical ultrasound imaging"). There are several existing tools available to researchers interested in using ultrasound to image small animals, including clinical imaging scanners, and specialized preclinical imaging systems. These tools enable either two-dimensional (2D) cross sections of tissue or small three-dimensional (3D) volumes of tissue. As used herein, "small subvolumes" do not encompass a significant portion of the animal's anatomy (e.g., >50% by volume). The consequence of this is comparisons between image acquisitions captured at different times are difficult to make, since relative orientations between tissue structures are unknown, as transducer orientation and scan angle is very difficult to identically recapitulate at two separate timepoints. This problem of one-to-one mapping between timepoints is further exacerbated when tissue structures are not in the same relative positions in the image data, which can be caused by multiple factors including: 3D non-linear warping that takes place when tissues are distended by physical contact between an ultrasound transducer and the tissue, a tumor growing and changing the tissue morphology within its neighborhood, one or more tumors arriving between timepoints, animal weight gain or loss, causing a spatial re-scaling between corresponding anatomical points, etc.

Accordingly, apparatuses, systems, and methods that circumvent these current deficiencies of preclinical ultrasound imaging are disclosed, which allow widefield imaging of tissue volumes. The apparatuses, systems, and methods may allow over 50% of a subject's body to be imaged, and thus better enable longitudinal comparisons. In addition to allowing an increased field of view, the quality of the image data will be improved by the apparatuses, systems, and methods described herein, as these apparatuses, systems, and methods may allow spatial compounding approaches to be implemented. Furthermore, these apparatuses, systems, and methods do not require direct contact to be made between transducer and tissue, and thus no tissue warping may be caused by the image acquisitions of these apparatuses, systems, and methods, better enabling image registration.

In addition, the present subject matter is based on the idea that one can acquire both anatomical and functional images with the same device or platform. Ultrasound imaging may be used to acquire anatomical images using the presently disclosed apparatus, system and method, while the specific functional imaging modality (SPECT, PET, optical, photoacoustics, optoacoustics, fluorescence, bioluminescence, cryoimaging, etc.) may be coupled with the presently disclosed apparatuses, systems, and methods for a complimentary approach to preclinical image acquisition.

In some aspects, the present subject matter described herein is directed to acquiring whole-body images with preclinical ultrasound imaging. Most current clinical and preclinical ultrasound transducers acquire 2D images and display the result on a computer monitor. To buildup a 3D image volume, the user must move the probe or transducer in a controlled manner to make a stack of 2D images into a cohesive 3D volume. Currently, there are already available methods of moving a transducer in a single linear path to construct a single subvolume of a target (i.e., an image of a preclinical animal model's tumor). Notably, the present subject matter proposes to extend this idea over a significantly larger area by using apparatuses, systems, and methods comprising two or more one-dimensional (1D) linear motion stages capable of controlling a spatial position of at least one ultrasound transducer's position to enable a cohesive volumetric image to be formed from a series of 2D images using the spatial coordinates of the ultrasound transducer's spatial position. It is contemplated that 3D functional images may be acquired using a functional imaging modality to fuse with the anatomical image acquired using the apparatuses, systems, and methods described herein. In some aspects, the 3D functional images may also be acquired using said apparatuses, systems, and methods disclosed herein. Any major functional imaging technique may be used to acquire the 3D images, such as, for example, photoacoustics, optoacoustics, fluorescence, bioluminescence, PET, SPECT, cryoimaging, x-ray, MRI, etc.

FIGS. 1A-1B and 2A-2B are illustrations of two separate, exemplary embodiments of apparatuses for preclinical imaging of a subject where the ultrasound transducer is configured to move relative to both the subject and the reservoir. In either embodiment, the apparatus may comprise an ultrasound transducer or plurality of ultrasound transducers, at least one motion stage, and/or one or more individual platforms. In some aspects, at least one motion stage may comprise a combination of at least one linear motion stage and at least one rotational computerized stage for moving and supporting ultrasound transducer(s) (see, e.g., FIG. 3). In a first example, at least one transducer may be configured to scan a subject at position(s) above the subject (see, e.g., FIGS. 1A and 1B), while in a second example, a transducer may be configured to scan a subject at position(s) below the subject (see, e.g., FIGS. 2A-2B).

Referring to FIG. 1A, an apparatus, generally designated 100A, may be configured such that at least one transducer 102A is movable via an actuating arm (see, e.g., 312, FIG. 3) relative to both subject S positioned on a platform 104A and a reservoir 106A. As illustrated in FIG. 1A, reservoir 106A may be in the form of a stand-alone tank with structured walls to contain a coupling medium 108A, which may be liquid or gel-based. The walls of reservoir 106A may be removable, either by complete detachment from platform 104A, or by mechanically lowering platform 104A into a recessed cavity. A coupling medium impermeable membrane 110 may be disposed between subject S and coupling medium 108A to provide a seal between the two.

Figure 1B:
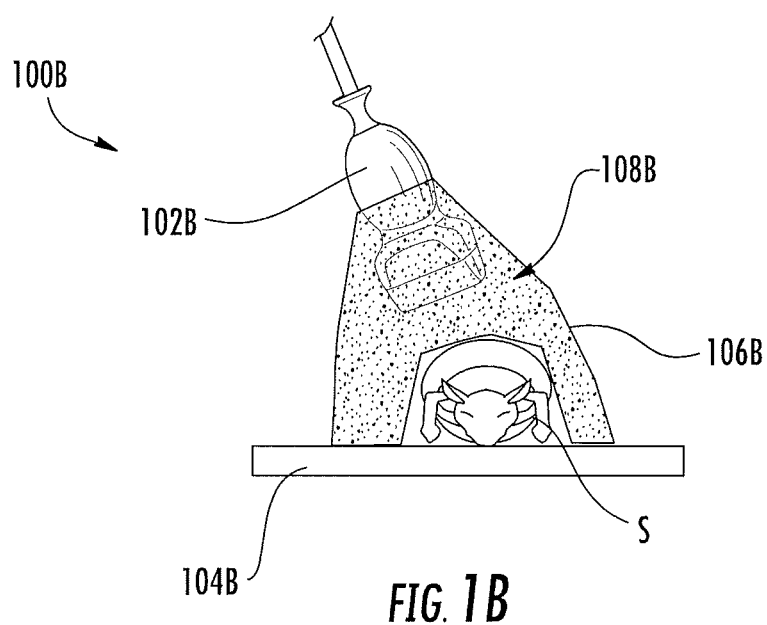
FIG. 1B is a front view illustrating an exemplary embodiment of an apparatus including a reservoir membrane for preclinical ultrasound imaging of a subject, wherein an imaging transducer scans substantially above the subject, according to the subject matter disclosed herein.

Alternatively, as illustrated in FIG. 1B, an apparatus, generally designated 100B, may be configured in a manner similar to that of FIG. 1A with a transducer 102B movable via an actuating arm (see, e.g., 312, FIG. 3) relative to both a subject S positioned on a platform 104A and a reservoir 106A. However, in comparison with FIG. 1A, reservoir 106B may be in the form of a bag that hangs from the same actuating arm. In this embodiment, a coupling medium impermeable membrane does not need to be utilized because reservoir bag 106B acts as its own coupling medium impermeable membrane in between a coupling medium 108B and subject S. In addition, as illustrated in FIG. 1B, reservoir bag 106B may be coupleable to the one or more individual platform 104B. For example, reservoir bag 106B may be anchored to platform 104B supporting subject S. Consequently, where an apparatus is configured to include a reservoir, the reservoir may, itself, either act as a partition between the subject being imaged and the coupling medium or may further comprise a coupling medium impermeable membrane between the coupling medium and the subject being imaged to prevent the subject from being submerged in the coupling medium.

Figure 7:
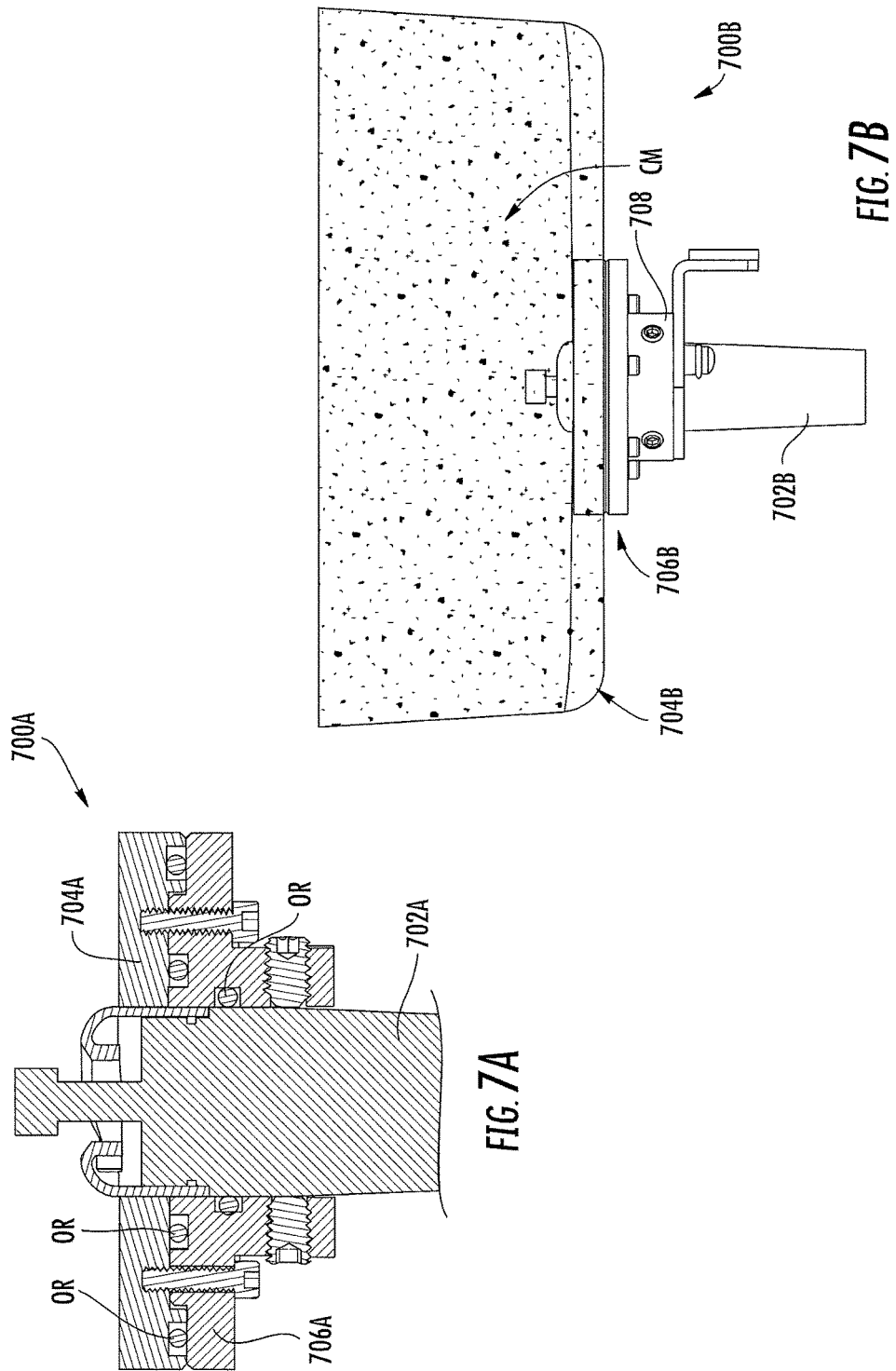
FIG. 7A is a cross-sectional view illustrating an exemplary cross-coupling clamp disposed between a transducer and a rigid reservoir for an exemplary embodiment of an apparatus for preclinical ultrasound imaging of a subject according to the subject matter disclosed herein.
FIG. 7B is a cross-sectional view illustrating an exemplary cross-coupling clamp disposed between a transducer and a reservoir membrane for an exemplary embodiment of an apparatus for preclinical ultrasound imaging of a subject according to the subject matter disclosed herein.

As in FIGS. 1A and 1B, where a reservoir is configured such that a separate or integral a coupling medium impermeable membrane, or other type of partition, is necessary to separate the subject from being imaged from the coupling medium, sufficient downward pressure may be generated by the coupling medium to ensure that the seal between the membrane and platform is coupling medium impermeable. In some aspects, the membrane may be sealed to the platform using a rectangular rigid frame, or other geometrically shaped frame, bearing magnetic material which may be activated by alternating a polarity of magnets disposed below the platform on which the subject is positionable. In some aspects, the membrane maybe sealed to the platform by using a rectangular rigid frame, or other geometrically shaped frame, which may be mechanically forced downward by one or more clamps (see, e.g., FIGS. 7A-7B). In some aspects, the membrane may be sealed to the platform by using a rectangular rigid frame, or other geometrically shaped frame, which may be mechanically forced downward via a vacuum seal. Regardless of the specific method for generating downward pressure between the membrane and animal platform, the two components can be quickly unattached for quick removal of the membrane after the imaging session has concluded.

In another alternative, not shown, a reservoir containing coupling medium is not needed in the apparatus in order to perform preclinical ultrasound imaging of a subject. For example, a REXOLITE® stage may be used, instead, and the at least one transducer may be scanned across the stage.

Figure 2A:
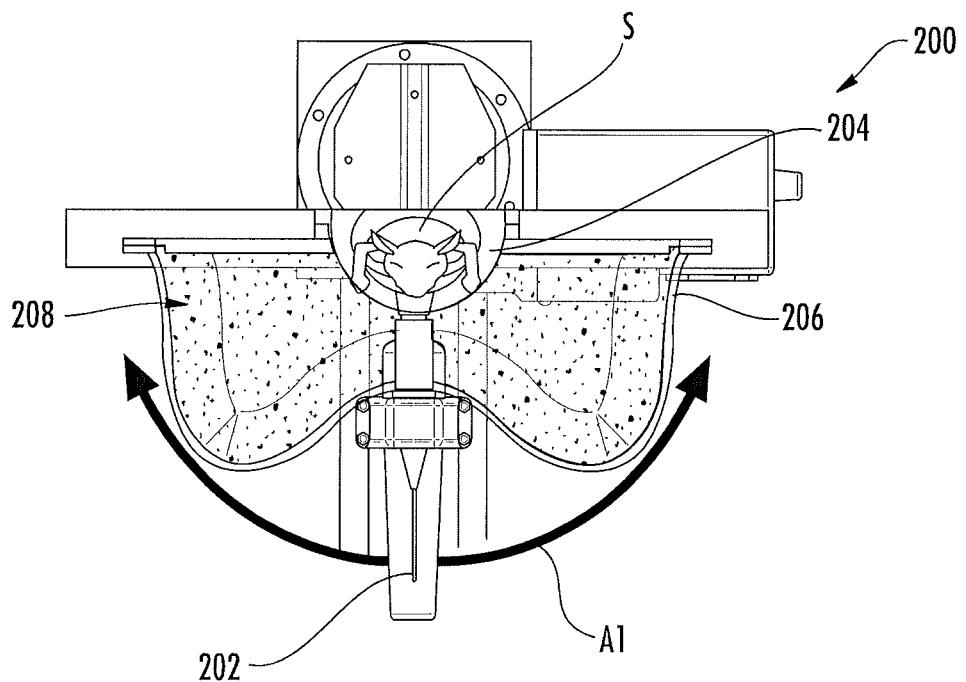
FIG. 2A is a front view illustrating an exemplary embodiment of an apparatus for preclinical ultrasound imaging of a subject, wherein an imaging transducer scans substantially below the subject, according to the subject matter disclosed herein.

Referring to the above-referenced exemplary embodiment, FIG. 2A illustrates an apparatus, generally designated 200, comprising at least one transducer 202 positioned below a subject S that is configured to movably scan subject S from underneath the subject. For example, transducer 202 may scan subject S below a platform 204 on which the subject is placed. In some aspects, apparatus 200 may comprise a reservoir 206 in the form of a stand-alone tank or a bag, as discussed above. For example, reservoir 206 may be in the form of an acoustic coupling reservoir. As illustrated in FIG. 2A, reservoir 206 is in the form of a bag that contains a coupling medium 208. Reservoir 206 may be suspended from or otherwise affixed to platform 204. In such a configuration, a coupling medium impermeable membrane does not need to be utilized because the acoustic coupling reservoir acts as its own coupling medium impermeable membrane in between coupling medium 208 and subject S. In the alternative, apparatus 200 does not need reservoir 206 containing coupling medium 208 in order to perform preclinical ultrasound imaging.

Figure 2B:
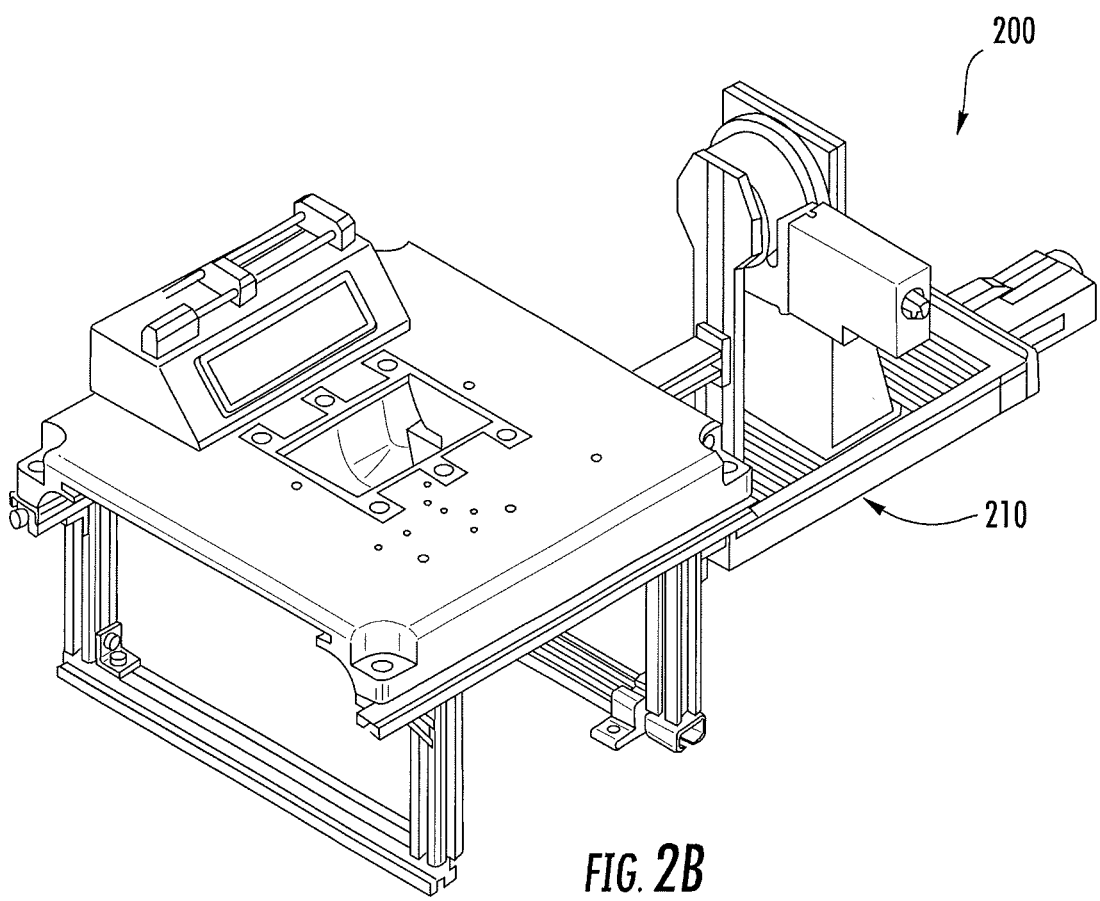
FIG. 2B is a perspective view illustrating the exemplary embodiment of FIG. 2A.

Still referring to the second embodiment, FIG. 2B illustrates apparatus 200 from a perspective view, where at least one motion stage, generally designated 210 is visible. Motion stage 210 may be connectably attached to transducer 202 and may thus move transducer 202 (not visible in FIG. 2B) relative to an imaging area underneath a subject, as indicated by arrow $A_1$ in FIG. 2A. Although arrow $A_1$ in FIG. 2A is illustrated as moving in a semi-circular manner relative to subject S, it is contemplated that motion stage 210 may also move transducer 202 substantially horizontally, vertically, etc., with regard to subject S, which will be described in greater detail below.

Figure 3:
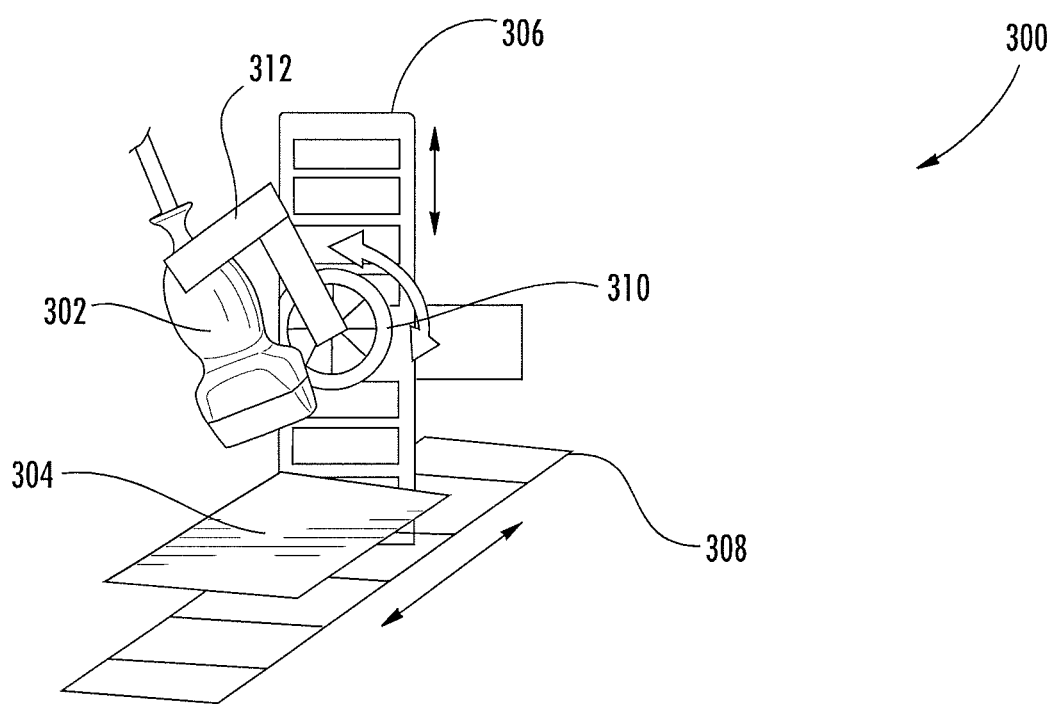
FIG. 3 is a front view illustrating a rotational stage and two linear stages of an apparatus for preclinical ultrasound imaging of a subject according to the subject matter disclosed herein.

Still referring to an embodiment of an apparatus, system, and/or method of preclinical imaging of a subject where a transducer moves relative to both a subject and a reservoir, FIG. 3 illustrates an exemplary apparatus 300 including one transducer 302 movable relative to a platform 304 and a reservoir (not illustrated in this Figure). Notably, more than one transducer moveable in a similar or different manner to the one illustrated in FIG. 3 may also be included in the apparatuses, systems, and/or methods described herein.

In FIG. 3, transducer 302 may be movable about three stages, one of which is rotational and the other two being linear, and each comprising its own individual axis on which transducer 302 may be independently movable. For example, the individual axes of the three stages may include a y-axis motion stage 306, a z-axis motion stage 308, and a Θ-axis motion stage 310, y-axis motion stage 306 and z-axis motion stage 308 allowing for linear movement of transducer 302 and Θ-axis motion stage 310 allowing for rotational movement of transducer 302. Notably, there may be more stages or fewer stages, as well, for different degrees of movement of transducer 302. In some embodiments, transducer 302 may be positioned on an actuating arm 312 that is coupled to the three stages. Thus, movement of each of the three stages individually moves the position of actuating arm 312 along that axis with respect to a subject, and thereby translates into movement of transducer 302 into various spatial positions relative to platform 304. For example, motion stages 306-310 may be configured to position transducer 302 above a subject in order to scan the subject from above (i.e., above platform 304), while the motion stages 306-310 may also be configured to position transducer 304 below the subject in order to scan the subject from below (i.e., below platform 304). The ability to move each of the three stages 306-310, independently, enables apparatus 300 to be configured in either the first exemplary position (i.e., FIGS. 1A-1B) or the second exemplary position (i.e., FIGS. 2A-2B) of the apparatus described above.

In some aspects, transducer 302 may be moved in any of the three directions (x, y, Θ) manually and/or automatically using a motion control system associated with a computing platform (see, e.g., FIG. 12), such that transducer 302 is movable 360 degrees around a subject positioned on platform 304. For example, a motion control system may enable one or more users to enter a mode of operation (e.g., jogging mode) where a spatial position of transducer 302 is controlled by a computing platform, or an external joystick or keypad, and transducer 302 is moved to a specified location. In some aspects, a spatial position or positions of transducer 302 may be determined a priori by a computing platform in order to control the linear and rotational stages' 306-310 positions. Regardless, this mode may be useful for users wanting to explore tissue volume to locate features of interest in a subject. Consequently, movability of transducer(s) in the manner described above may enable whole-body images to be acquired by the disclosed apparatuses, systems, and/or methods, since the transducer(s) may be translatable around a body of a subject in order to acquire images at different and various angles.

Referring now to another embodiment, FIGS. 4-9 are illustrations of another exemplary embodiment of an apparatus and a system for preclinical imaging of a subject where an ultrasound transducer and a reservoir are configured to move together relative to a subject being imaged in comparison to the embodiments illustrated in FIGS. 1A-3, where a transducer is configured to move relative to both a subject and a reservoir.

Figure 4:
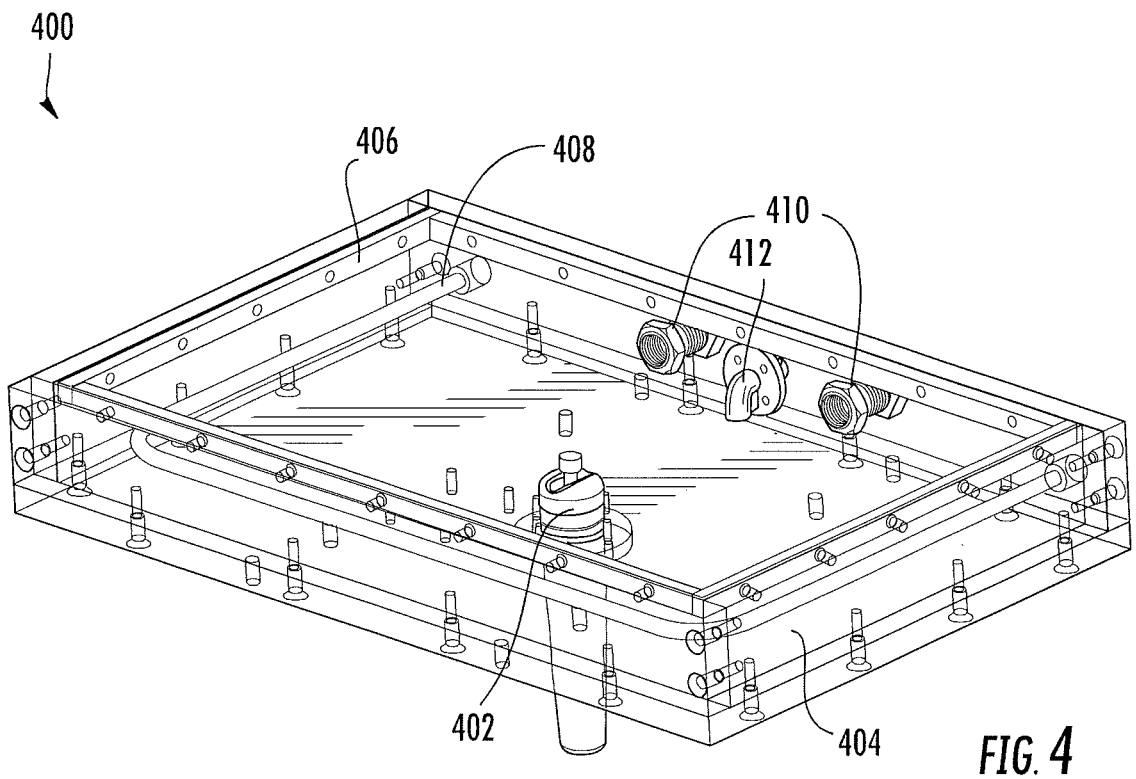
FIG. 4 is a perspective view illustrating an exemplary reservoir for an exemplary embodiment of an apparatus for preclinical ultrasound imaging of a subject according to the subject matter disclosed herein.

FIG. 4 illustrates a perspective view of an exemplary embodiment of an apparatus, generally designated 400, for preclinical imaging of a subject. Apparatus 400 may be configured with at least one movable transducer 402 that is coupled to a bottom surface of a reservoir 404. In some aspects, reservoir 404 may be a rigid box or stand-alone tank with structured walls rather than a flexible bag. For example, FIG. 4 illustrates reservoir 404 as a rigid, rectangular box having a bottom surface and four structured walls that are substantially perpendicular to the bottom surface of reservoir 404. Reservoir 404 may be composed of an acoustically attenuating material to limit reflection and reverberation of ultrasound waves during imaging. An orifice having a diameter sufficient to receive transducer 402 may be provided in the bottom surface of reservoir 404. In such a manner, transducer 402 may be introduced under reservoir 404 through the bottom surface and removably coupled to reservoir 404 via a mechanism (e.g., 706A, 706B, FIGS. 7A-7B). Thus, movement of transducer 402 once coupled to reservoir 404 results in movement of reservoir 404 relative to an imaging chamber on which a subject is placed (see, e.g., FIG. 9).

Although not illustrated in FIG. 4, a coupling medium impermeable membrane may be provided with respect to reservoir 404 in order to provide a seal between the coupling medium and a subject to be imaged, although it may be unnecessary for contact-free imaging. In order to retain the coupling medium impermeable membrane, reservoir 404 may include a spray skirt, or other similar mechanism, disposed around its perimeter. For example, as illustrated in FIG. 4, a spray skirt 406 is disposed along each of the side walls of reservoir 404 and is configured to retain a coupling medium impermeable membrane to create a seal between any coupling medium contained in reservoir 404 and a subject being imaged, above. Spray skirt 406 may be clamped, bolted, pinched, screwed, and/or otherwise brought into close contact with the inside surface of respective side walls on which spray skirt 406 is disposed, with the coupling medium impermeable membrane sandwiched in between spray skirt 406 and the side walls of reservoir 404 for a tight seal.

In some aspects, a heating mechanism may be disposed along an interior surface of one or more side walls of reservoir 404. For example, reservoir 404 may comprise a U-shaped thermal rod 408 disposed along three of the side walls for immersion heating. In this manner, the coupling medium may be heated while it is already contained within reservoir 404. In some aspects, the temperature of the coupling medium within reservoir 404 may be adjusted (e.g., either automatically or using real time user input) via an input to U-shaped thermal rod 408. For example, a feedback controller (e.g., a proportional-integral-derivative controller) may be used for passively regulating the temperature of the coupling medium within reservoir 404 to a desired temperature, e.g., a body temperature of a subject, throughout an imaging session.

Further temperature adjustment functionality is also contemplated for reservoir 404. In some aspects, where a coupling medium impermeable membrane is provided, a coupling medium may be heated outside of reservoir 404. For example, reservoir 404 may comprise an attachable pump (not shown) to circulate liquid between reservoir 404 and a separate temperature controlled reservoir where the coupling medium is regulated to a desired temperature. In some aspects, a surface of reservoir 404 may be heated directly from an outside, rather than through thermal rod 408, to passively heat coupling medium. For example, a heating lamp or heating plate may be used. Temperature adjustment functionality for heating a coupling medium disposed within a reservoir may also be implemented in any other manner and in any of the other embodiments described herein, (i.e., a reservoir configured as in 106A, 106B, 206).

One or more ports 410 may be provided in one or more side walls of reservoir 404. As illustrated in FIG. 4, two ports 410 are provided in a first side wall of reservoir 404. Ports 410 may provide an entry and/or exit for sensors. In some aspects, a sensor may be provided for apparatus 400 to detect a temperature, height, presence, etc., of a coupling medium within reservoir 404. For example, one or more thermocouples (not shown) may be threaded through port(s) 410 to measure a temperature of a coupling medium. The thermocouple may be used as feedback to an acquisition model associated with a computing platform that may implement control software to adjust the temperature of the reservoir appropriately, using, for example, thermal rod 408. Ports for providing sensors of any type into a reservoir may also be implemented in any of the other embodiments described herein, (i.e., a reservoir configured as in 106A, 106B, 206).

In some aspects, reservoir 404 may also comprise an input/output for delivering and/or draining reservoir 404 of a coupling medium. For example, FIG. 4 illustrates an input/output 412 disposed in between the two ports 410 on the first side wall that is configured to fill/drain reservoir 404 with coupling medium. One or both filling and draining reservoir 404 may be controlled manually or automatically by a computing platform associated with apparatus 400. An input/output for delivering and/or draining a reservoir may also be implemented in any of the other embodiments described herein, (i.e., a reservoir configured as in 106A, 106B, 206). Notably, it may be desirable to drain water from a reservoir after each imaging session in order to avoid damaging the transducer.

Figure 5:
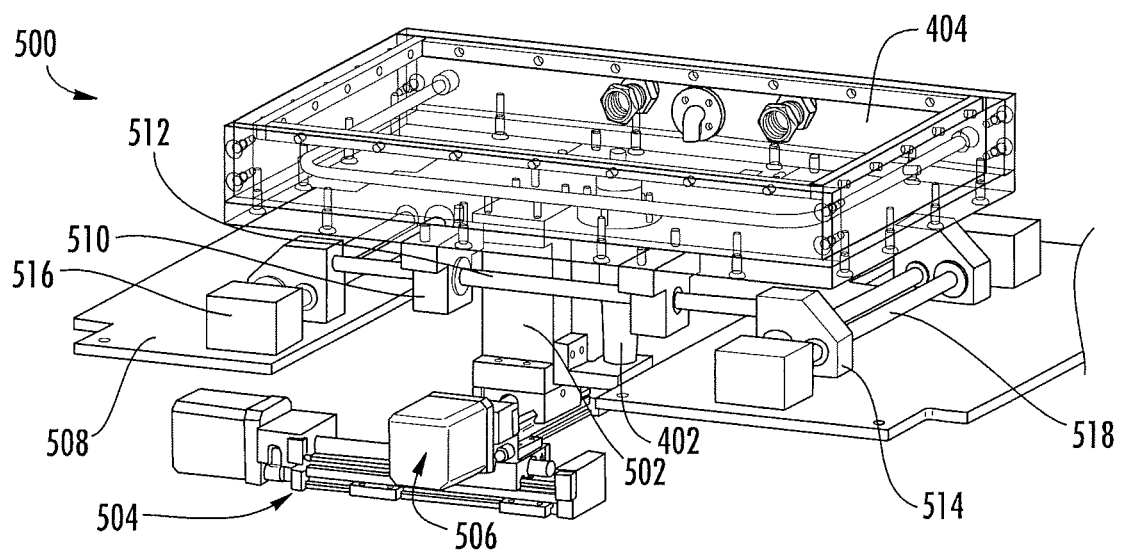
FIG. 5 is a perspective view illustrating an exemplary reservoir, support structure, and x and y-axis motion stages for an exemplary embodiment of an apparatus for preclinical ultrasound imaging of a subject according to the subject matter disclosed herein.

Referring now to FIG. 5, a front perspective view of an apparatus, generally designated 500, which includes a transducer 402 and a reservoir 404 as described above is provided. Apparatus 500 includes an I-beam 502 that connects both transducer 402 and reservoir 404 to an x-axis motion stage 504 and a y-axis motion stage 506, and a U-shaped platform 508 with one or more blocks 510 for supporting the extra weight from reservoir 404. In comparison with embodiments of apparatuses, systems, and methods for preclinical imaging where the transducer moves relative to both a subject and a reservoir, in the embodiment provided in FIG. 5, the transducer and the reservoir move simultaneously relative to a subject. As a result, the motion stages that are configured to move the transducer must be configured to simultaneously translate a reservoir containing a quantity of coupling medium in two dimensions.

In some aspects, I-beam 502 comprises a non-weight bearing structure that may be configured to couple reservoir 404 to motion stages 504, 506. For example, I-beam is rigidly fixed to a bottom surface of reservoir 404 at a first end and is rigidly fixed to both motion stages 504, 506 at a second end. In some aspects, I-beam 502 may also comprise a ring (e.g., 602, FIG. 6) that is configured to rigidly receive a bottom surface of transducer 402. For example, transducer 402 may be inserted into an orifice in a bottom surface of reservoir 404 and then rigidly received by the ring of I-beam 502. In this manner, transducer 402 is retained in a rigid relationship (i.e., precise spatial location) relative to reservoir 404 during translation of I-beam 502 along one or both of the x-axis or the y-axis.

X-axis motion stage 504 and y-axis motion stage 506 provide linear translation of transducer 402 and reservoir 404 via translation of I-beam 502. Each of x-axis motion stage 504 and y-axis motion stage 506 are independently movable relative to a stationary subject (not shown in this Figure) in order to scan the subject from a variety of desired spatial positions in a horizontal plane. Thus, transducer 402 may be moved in x, y manually and/or automatically using a motion control system associated with a computing platform (see, e.g., FIG. 12), such that transducer 402 is movable in a horizontal plane relative to a subject positioned above reservoir 404. For example, a motion control system may enable one or more users to enter a mode of operation (e.g., jogging mode) where a spatial position of transducer 402 is controlled by the computing platform, or an external joystick or keypad, and transducer 402 is moved to a specified location via motors controlling x, y stages 504, 506. In some aspects, a spatial position or positions of transducer 402 may be determined a priori by the computing platform in order to control the linear stages' 504-506 positions. Regardless, this mode may be useful for users wanting to explore tissue volume to locate features of interest.

In order to support reservoir 404 and coupling medium contained within, apparatus 500 includes a weight bearing apparatus. In some aspects, the weight bearing apparatus may comprise a plurality of blocks configured to distribute the weight across a platform, a suspension configuration from above the reservoir, rollers below the reservoir, or other strain relieving methods. As illustrated in FIG. 5, the weight bearing apparatus may comprise platform 508, contact blocks 510, rods 512, sleeve bearing blocks 514, and anchored corner blocks 516. Platform 508 may comprise a U-shaped platform with a center removed to receive I-beam 502 and transducer 402. Platform 508 may be composed of a rigid material, such as aluminum.

In some aspects, one or more contact blocks 510 may be fixedly attached to a bottom surface of reservoir 404. For example, four T-shaped contact blocks 510 may be fixedly attached to reservoir 404, where two blocks 510 are provided on one longitudinally extending side and two blocks 510 are parallelly provided on an opposing longitudinally extending side of a bottom surface of reservoir 404 so that they are not in contact with platform 508. In some aspects, screws, bolts, and/or any other type of fastener may be used to fixedly attach contact blocks 510 to reservoir 404. Each of contact blocks 510 may be provided with a through-hole through which greased rods 512 may be slideably threaded. Greased rods 512 may terminate at each end in sleeve bearing blocks 514 suspended over platform 508. For example, a first end of a first rod 512 may be fixed in a first sleeve bearing block 514 and be slideably threaded through two contact blocks 510 disposed on a first longitudinally extending side of a bottom surface of reservoir 404 and a second end of the first rod 512 may terminate in a second sleeve bearing block 514, while a first end of a second rod 512 may be fixed in a third sleeve bearing block 514 and be slideably threaded through two contact blocks 510 disposed on a second, opposing longitudinally extending side of the bottom surface of reservoir 404 and terminate in a fourth sleeve bearing block 514. The first and third sleeve bearing blocks and the second and fourth bearing blocks 514 may be parallel to one another, while the first and second bearing blocks and the third and fourth bearing blocks 514 may also be parallel to one another. In this way, when x-axis motion stage 504 translates reservoir 404 along the x-axis, contact blocks 510 translate along rods 512 a corresponding magnitude and direction along the x-axis.

Each of sleeve bearing blocks 514 may be suspended over platform 508 by one or more greased rods 518 being provided through through-holes in each of sleeve bearing blocks 514 and terminating at each end in anchored corner blocks 516 fixed onto platform 508. Axes of through-holes through which greased rods 518 extend in sleeve bearing blocks 514 are substantially orthogonal to a surface in sleeve bearing blocks 514 at which ends of rods 512 terminate. For example, a first end of a first rod 518 may be fixed in a first anchored corner block 516 and be slideably threaded through two sleeve bearing blocks 514 and a second end of the first rod 518 may terminate in a second anchored corner block 516 and a first end of a second rod 518 may be fixed in a third anchored corner block 516 and be slideably threaded through two sleeve bearing blocks 514 and terminate in a fourth anchored corner block 516. Where there are more than two rods 518 in each of sleeve bearing blocks 514, rods 518 may extend in parallel to one another. The first and third anchored corner blocks and the anchored corner blocks 516 may be parallel to one another, while the first and second anchored corner blocks and the third and fourth anchored corner blocks 516 may also be parallel to one another. In this way, when y-axis motion stage 506 translates reservoir 404 along the y-axis, sleeve bearing blocks 514 translate along rods 518 a corresponding magnitude and direction along the y-axis.

Figure 6:
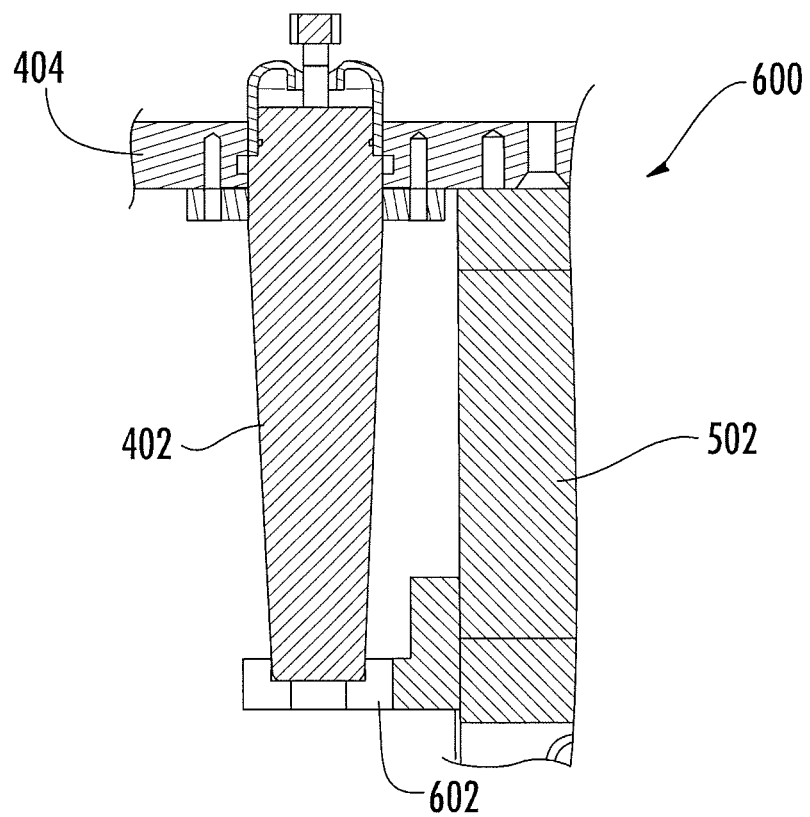
FIG. 6 is a cross-sectional view illustrating an exemplary transducer aligned with an I-beam for an exemplary embodiment of an apparatus for preclinical ultrasound imaging of a subject according to the subject matter disclosed herein.

Now referring to FIG. 6, a cross-sectional view of an exemplary embodiment of an apparatus, generally designated 600, including transducer 402, reservoir 404, and I-beam 502 as described above, is provided. As noted, I-beam 502 may comprise a ring 602 configured to rigidly receive a bottom surface of transducer 402, while a top surface of transducer 402 may be securely received in a bottom surface of reservoir 404. For example, ring 602 may comprise an indented bottom surface sized to receive a bottom surface of transducer, such that transducer 402 may be able to be stabilized and cannot be misaligned. In other examples, ring 602 may be configured to retain transducer 602 using other contemplated methods. Regardless, transducer 402 may be rigidly aligned (i.e., in a precise spatial location) relative to reservoir 404 during translation of I-beam 502 along either the x-axis or the y-axis.

While a bottom surface of transducer 402 may be secured to ring 602 of I-beam 502, a top surface of transducer 402 may be coupled to a bottom surface of reservoir 402 in a substantially water-tight manner. Now referring to FIGS. 7A-7B, a coupling mechanism may be provided which may be configured to act as a seal between the transducer and the reservoir and thereby prevent substantial leakage therebetween. In FIG. 7A, a cross-sectional view of a first embodiment, generally designated 700A, provides for a transducer 702A and a reservoir 704A similar to transducer 402 and reservoir 404 described with regard to earlier embodiments. For example, reservoir 704A is a rigid tank, rather than a bag reservoir (see, e.g., 704B, FIG. 7B). In some aspects, a coupling mechanism or cross-coupling clamp 706A, may be an annular clamp disposed around an outer circumference of transducer 702A having a top surface substantially abutting a bottom surface of reservoir 704A. Clamp 706A may comprise a radial or inward pressure to seal around transducer 702A, using, for example, a fastening element. Upward clamping pressure may be applied from clamp 706A towards reservoir 704A to seal between transducer 702A and reservoir 704A, using similar fastening elements. As illustrated in FIG. 7A, two fastening screws are used to provide inward pressure on clamp 706A, while two fastening screws are used to provide upward clamping pressure on reservoir 704A. One or more o-rings, generally designated OR, may be utilized to provide radial pressure on transducer 702A. For example, three o-rings OR may be utilized as illustrated in FIG. 7A. However, using o-rings OR may cause slight misalignment of transducer 702A in which case a secondary method of positioning transducer 702A may be required. One such secondary method may be, for example, to include a secondary stabilization point at a distal or bottom end of transducer 702A.

In some aspects, a coupling mechanism for a reservoir comprising a flexible bag is provided. FIG. 7B is a second embodiment, generally designated 700B, of a transducer 702B and a reservoir 704B that differs from the first embodiment 700A in that reservoir 704B is a flexible bag or membrane containing coupling medium CM. Additionally, a coupling mechanism or cross-coupling clamp 706B may be an annular clamp disposed around an outer circumference of transducer 702B having a top surface substantially abutting a bottom surface of reservoir 704B in order to add additional clamping pressure onto coupling medium CM contained within reservoir 704B. In such a manner, clamp 706B allows transducer 702B to enter through a bottom of reservoir 7046 without leakage of coupling medium CM. A bracket 708 provided on a side of clamp 7066 may enable movement of transducer 702B.

Figure 8:
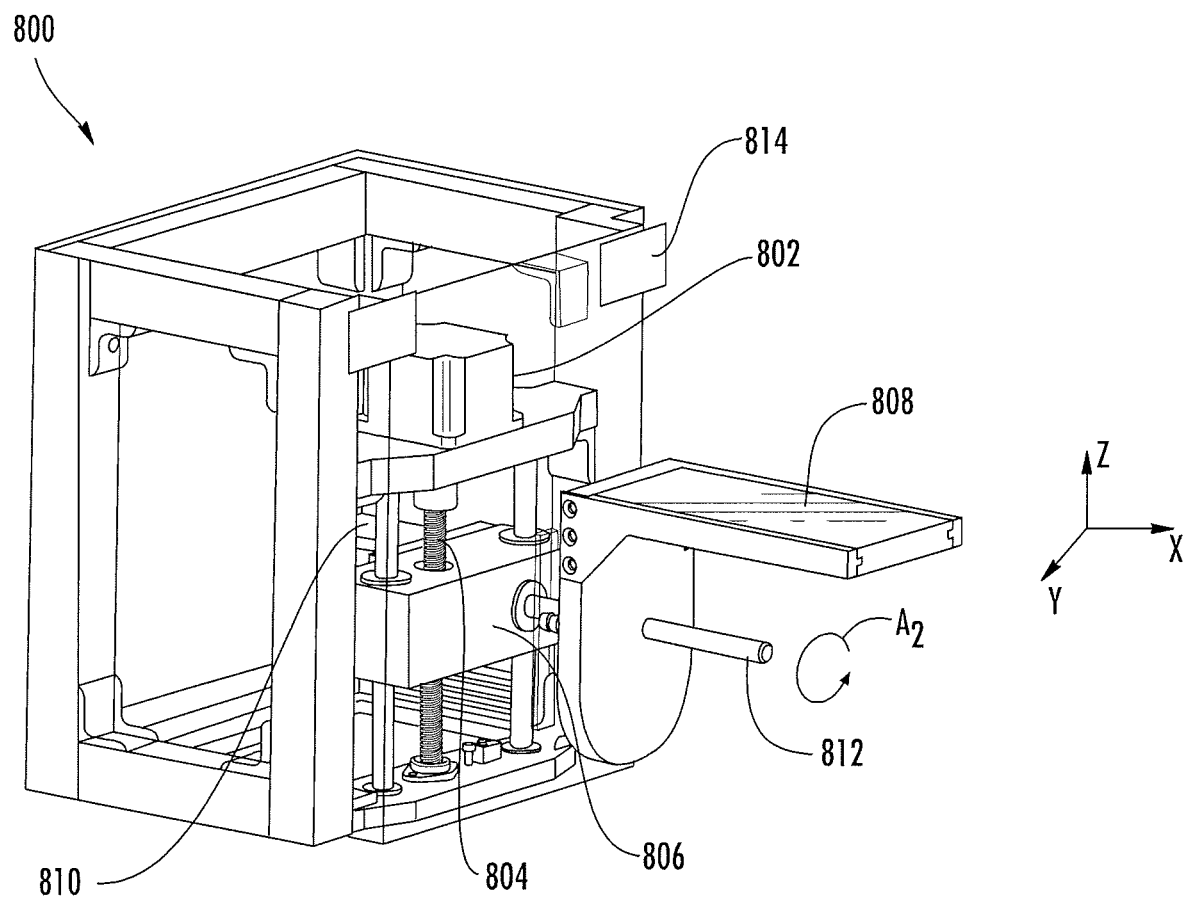
FIG. 8 is a perspective view illustrating an exemplary z-axis and rotational motion stage for an exemplary embodiment of an apparatus for preclinical ultrasound imaging of a subject according to the subject matter disclosed herein.

Now referring to FIG. 8, a perspective view of an apparatus, generally designated 800, for providing z-axis and rotational movement of a subject into an imaging chamber over a reservoir, such as reservoir 404 in FIG. 4, is provided. Where apparatus 800 is used in conjunction with an apparatus, such as apparatus 500 (see, e.g., FIG. 5), the resulting configuration will be an apparatus such as apparatus 900, FIG. 9, where apparatus 800 is provided above apparatus 500 in the z-axis.

Z-axis movement of apparatus 800 may be achieved by a z-motion stage comprising a primary motor, generally designated 802, which is configured to drive vertical motion of a lead screw 804 along the z-axis on which a middle block 806 is rotatingly attached and coupled to a platform 808 on which a subject may be placed. In this manner, motor 802 may drive lead screw 804 either clockwise or counterclockwise, which will in turn drive middle block 806, and platform 808, either up or down in a z-axis direction along lead screw 804. Alternatively, motor 802 may drive a pulley system (not shown) in order to move platform 808 along the z-axis direction. Where apparatus 800 is configured to be disposed over a reservoir having a transducer disposed therein, as in any of the configurations described above, a subject positioned on platform 808 may be automatically raised and/or lowered into an imaging chamber over the reservoir through actuation of motor 802.

Notably, platform 808 is advantageously configured to be rotational about an x-axis, such that a subject placed belly up on platform 808 may be automatically rotated 180 degrees into a belly down position relative to an x-plane as the platform is lowered. More particularly, a rotational motion stage comprising a secondary motor, generally designated 810, may be utilized to actuate rotation of platform 808 via rotating a rotational shaft 812 in either a clockwise or counterclockwise manner a predetermined number of degrees (e.g., 180 degrees). Alternatively, a rack and pinion (not shown) may be used to rotate platform 808. Arrow $A_2$ illustrates rotation of shaft 812 about the x-axis. In some aspects, primary motor system 802 and secondary motor system 810 may simultaneously be actuated so that platform 808 is lowered along the z-axis at a same time as the platform is being rotated from a first position (i.e., belly up position—illustrated in FIG. 8) to a second position (i.e., belly down position) about the x-axis. Conversely, primary motor system 802 and secondary motor system 810 may simultaneously be actuated so that platform 808 is raised along the z-axis at a same time as the platform is being rotated from the second position to the first position about the x-axis.

In some aspects, one or more stationary optical cameras 814 may be provided on apparatus 800. Cameras 814 may be linked to a computing platform that may be used to control motors 802, 810 such that images of a subject on platform 808 may be automatically acquired at specific intervals while the subject is being lowered and/or raised and/or rotated on platform 808. Advantageously, acquiring images during movement and/or rotation of a subject is advantageous for combining pre-clinical ultrasound imaging with other modalities, especially bioluminescence imaging, because images of the subject at a number of different angles may be beneficial in constructing one or more projections of the subject for surface mapping.

Figure 9:
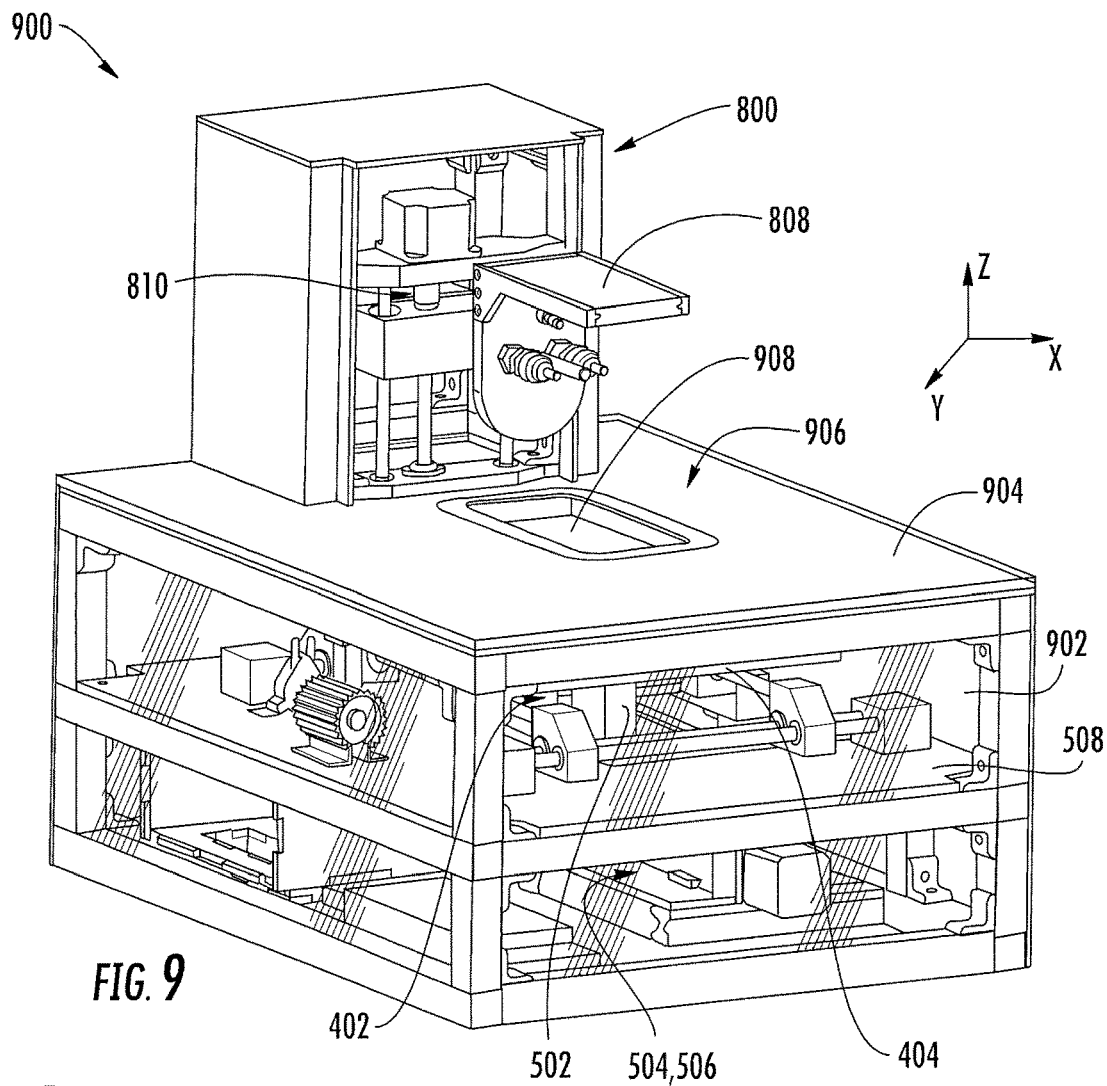
FIG. 9 is a perspective view illustrating an exemplary embodiment of an apparatus for preclinical ultrasound imaging of a subject according to the subject matter disclosed herein.

Referring now to FIG. 9, an apparatus generally designated 900 for preclinical ultrasound imaging of a subject is provided. Apparatus 900 comprises a plurality of components described in reference to FIGS. 4-8, including a transducer 402, reservoir 404, I-beam 502, x and y motion stages 504, 506, a z-motion stage 802, a rotational motion stage 810, and an animal platform 808. Reservoir 404 is coupled to x and y motion stages 504, 506 via I-beam 502 which, in turn, rigidly affixes transducer 402, to a bottom surface of reservoir 404, as described in FIGS. 4-7A. A removable housing 902 is provided to encase transducer 402, reservoir 404, I-beam 502, x and y motion stages 504, 506, as well as other components of apparatus 900. Removable housing 902 may be composed of a rigid material to add stability to apparatus 900 and may be removable in parts so that apparatus may be quickly assembled and disassembled, as necessary.

In some aspects, removable housing 902 may comprise a removable stage 904. Stage 904 may be configured as a removable lid to housing 902. For example, stage 904 is disposed over reservoir 404 such that a coupling medium disposed within reservoir 404 is substantially covered by stage 904. In this example, transducer 402, reservoir 404, I-beam 502, and x and y motion stages 504, 506 are disposed below stage 904, while z-motion stage 802, rotational motion stage 810, and animal platform 808 are provided above. In some aspects, stage 904 comprises an opening in which an imaging chamber 906 is defined. For example, the opening may be sized to receive platform 808 when platform 808 is in the lowered, second position. In such a position, platform 808 may be configured to be in close proximity to the coupling medium contained within reservoir 404. Accordingly, for example, a membrane 908 disposed on a bottom surface of imaging chamber 906 may be used as a barrier between coupling medium in reservoir 404 and imaging chamber 906 in order to protect a subject from the coupling medium contained within reservoir 404.

Accordingly, apparatus 900 may be utilized by an operator to translate transducer 402 along the x and y-axes by x and y motion stages 504, 506 and acquire pre-clinical ultrasound images of a subject positioned in a lowered, second position on platform 808. After acquisition of pre-clinical ultrasound images is complete, platform 808 may be raised and rotated back into a first position away from imaging chamber 906. Stage 904 may be removed and housing 902 may be disassembled in order to, for example, drain the coupling medium from reservoir 404 and/or remove transducer 402.

Figure 10:
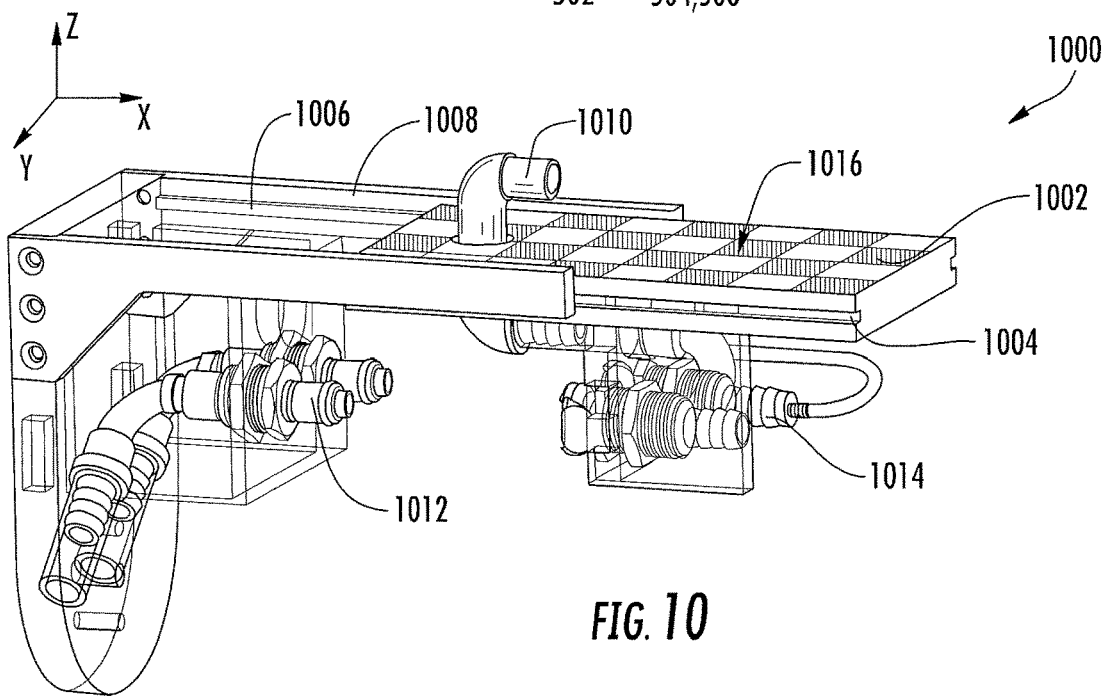
FIG. 10 is a perspective view illustrating an exemplary subject transfer platform for an exemplary embodiment of an apparatus for preclinical ultrasound imaging of a subject according to the subject matter disclosed herein.

Referring now to FIG. 10, an exemplary embodiment of a subject transfer platform, generally designated 1000, is provided. Specifically, subject transfer platform 1000 may be similar to platform 808 (FIG. 8) and may be configured to allow registration of images acquired during preclinical ultrasound imaging of a subject to other imaging modalities via one or more fiducial landmarks. Subject transfer platform 1000 may comprise a cassette 1002 that may be slidable and/or removable with regard to a rigid structure, such that cassette 1002 may be consistently and reliably positioned in a same spatial position for each imaging session. In some aspects, cassette 1002 may be a transferable item that can transfer to any number of imaging modalities (e.g., bioluminescence, cryoimaging, etc.)

As illustrated in FIG. 10, for example, cassette 1002 may be slideable along a groove 1004 that corresponds in width to a protrusion 1006 extending in each of a pair of guide rails 1008 in platform 1000. Thus, cassette 1002 may be configured to be slid completely onto guide rails 1008 so that a first end of cassette 1002 is coplanar with first end of guide rails 1008 and a second end of cassette 1002 substantially abuts a far wall of platform 1000. Thus, guide rails 1008 may be used to ensure vertical and lateral alignment of cassette 1002 in platform 1000.

In some aspects, cassette 1002 may comprise elements for interacting with a subject positioned thereon. For example, a nose cone 1010 for which a subject's nose is positioned, which is connectable and/or disconnectable with anesthesia tubes 1012 via valves 1014, is provided. Valves 1014 may be connected with nose cone 1010 and may be connectable and/or disconnectable to anesthesia tubes 1012 upon complete insertion of cassette 1002 in guide rails 1008. In FIG. 10, for example, cassette 1002 is illustrated in an intermediate position where the cassette is only partially slid onto guide rails 1008. Therefore, when cassette 1002 is completely slid onto guide rails 1008 so that cassette 1002 is considered completely inserted onto the guide rails, valves 1014 will be in a position to be connected to anesthesia tubes 1012 so that an uninterrupted flow of anesthesia may pass from anesthesia tubes 1012 to nose cone 1010. Additionally, connection of anesthesia tubes 1012 to nose cone 1010 acts as securing cassette 1002 at an appropriate position in a z-axis direction.

In other aspects, cassette 1002 may include an integrated heating mechanism (not shown) to ensure animal homeostasis during an imaging study. For example, cassette 1002 may include an embedded electrical heating pad, a recessed pocket for a chemical heating pad (e.g., a hand warmer, microwavable heating pad, etc.)

Cassette 1002 may also comprise one or more fiducial landmarks 1016 disposed on a top surface thereof. For example, in FIG. 10, cassette 1002 comprises a checkerboard pattern rendered in two distinct colors on a top surface of cassette 1002. A subject may be placed on this surface and then both optical images and ultrasound images may be acquired of the subject on the cassette 1002 against the fiducial landmarks 1016. For example, an optical camera (not shown in this Figure) may be utilized to acquire images of a subject and register those images with a modality other than ultrasound in order to provide more accurate and/or precise 2D or 3D images.

Figure 11A:
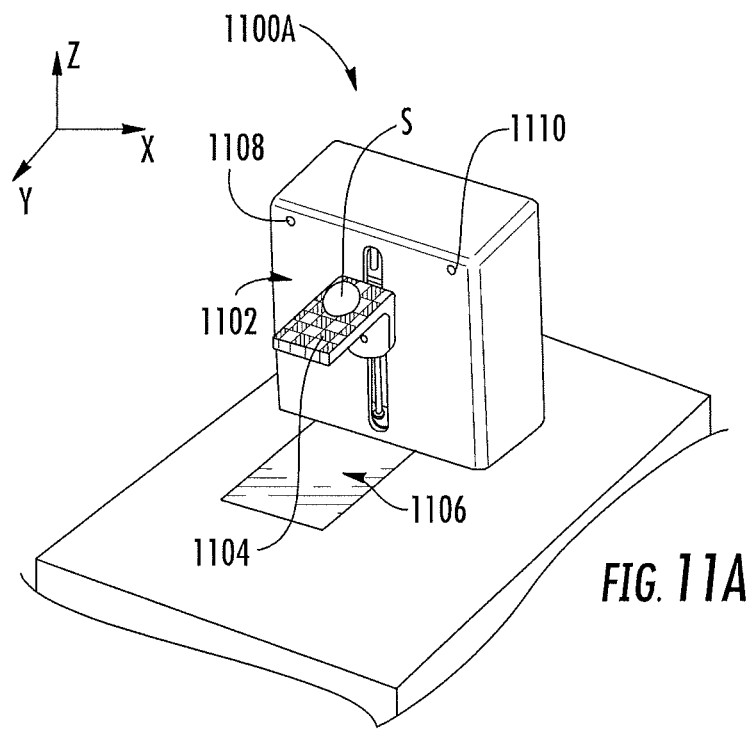
FIG. 11A is a line drawing illustrating an apparatus used in an exemplary process flow for generating an atlas using fiducial landmarks for preclinical ultrasound imaging of a subject according to the subject matter disclosed herein.

Referring now to FIGS. 11A-11G, computer generated images of an exemplary process flow for generating an atlas using fiducial landmarks, such as those depicted in FIG. 10, is illustrated. FIG. 11A illustrates a subject platform 1100A similar to 1000 illustrated in FIG. 10 and configured to include a subject S positioned thereon. Subject platform 1100A may be configured to include a cassette 1102 having one or more fiducial landmark 1104 disposed on a surface on which subject S is positioned. Fiducial landmark 1104 may comprise a checkerboard pattern rendered in two distinct colors similar to pattern 1016 in FIG. 10. Cassette 1102 may be movable with regard to platform 1100A in a z-axis and/or a rotational x-axis direction towards and/or away from an imaging chamber 1106, similar to the imaging chamber described in reference to FIG. 9, where a transducer (not shown) may be provided.

Figure 11B:
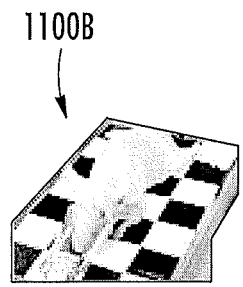
FIGS. 11B-11G are computer generated images illustrating an exemplary process flow for generating an atlas using fiducial landmarks for preclinical ultrasound imaging of a subject according to the subject matter disclosed herein.
Figure 11C:
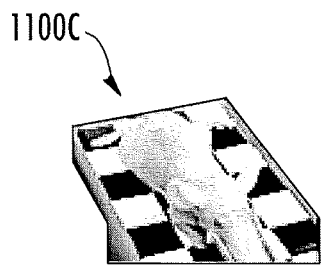

One or more optical cameras may be provided on animal platform 1100A. For example, two optical cameras 1108 and 1110 are provided in two disparate locations on platform 1100A. In some aspects, one or more optical camera 1108 and 1110 may be utilized to coarsely map (i.e., one to one spatially map) a spatial position of subject S on cassette 1102 in order to facilitate ultrasound imaging scan boundaries and subsequent positioning of subject S in later imaging sessions. One or more optical camera 1108 and 1110 may be actuated by a computing platform associated with platform 1100A to acquire images as cassette 1102 moves in either one or both a rotational and/or vertical manner towards imaging chamber 1106. FIGS. 11B-11C each illustrate exemplary computer generated images that may be acquired by each camera at a first time period. For example, FIG. 11B provides for image 1100B acquired by first camera 1108 during a first time period, while FIG. 11C provides for image 1100C acquired by second camera 1110 during the first time period. Thus, as can be seen from a comparison of images 1100B and 1100C, different angular views of subject S may be acquired at a same time period. Subsequent images may be acquired for each of cameras 1108 and 1110 for subsequent time periods.

Figure 11D:
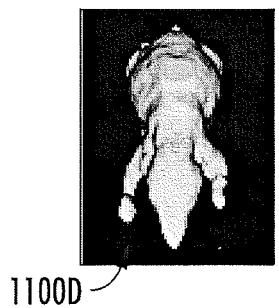

FIG. 11D illustrates a computer generated image, generally designated 1100D, of a topographic surface model formation based on the angular images acquired from cameras 1108 and 1110. Notably, the more images may be acquired at different time periods, the more precise the topographic surface models may be.

Figure 11E:
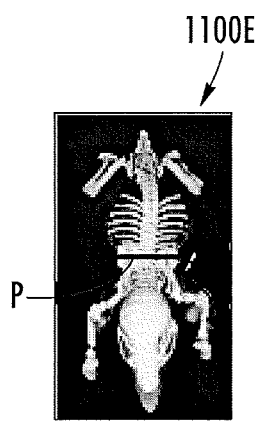

FIG. 11E illustrates a computer generated image, generally designated 1100E, of a surface model registered to a 3D atlas. The 3D atlas may be a 3D probability model of a subject that includes locations of specific features within a subject, e.g., a heart, stomach, bladder, etc. By registering a surface model of a subject to a 3D atlas of a generic subject, an operator may be able to determine an approximate location of where a specific organ is on a subject currently being imaged and then robotically translate a transducer in a preclinical ultrasound imaging system to that position relative to the platform, keeping in mind a surface geometry and contours of the subject For example, if the operator was interested in viewing the subject at line P the 3D atlas would enable precise positioning of the transducer at that point on the subject currently being imaged. In this manner, a 3D scan region of a region of interest (ROI) of a subject may also be displayed prior to acquisition of ultrasound images.

Figure 11F:
Figure 11G:
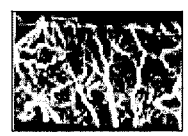

FIGS. 11F-11G each illustrate a computer generated image of a targeted ultrasound using the spatial positioning information achieved from the 3D atlas. Specifically, a screenshot of a targeted ultrasound image at line P in a B-mode scan 1100F and using acoustic angiography 1100G are illustrated in FIGS. 11F-11G, respectively.

Contact free imaging may thus be achieved by any of the embodiments illustrated in FIGS. 1A-11G, since the ultrasound probe may be coupled to the target without physical contact being made between the probe and the tissue of the subject.

Figure 12:
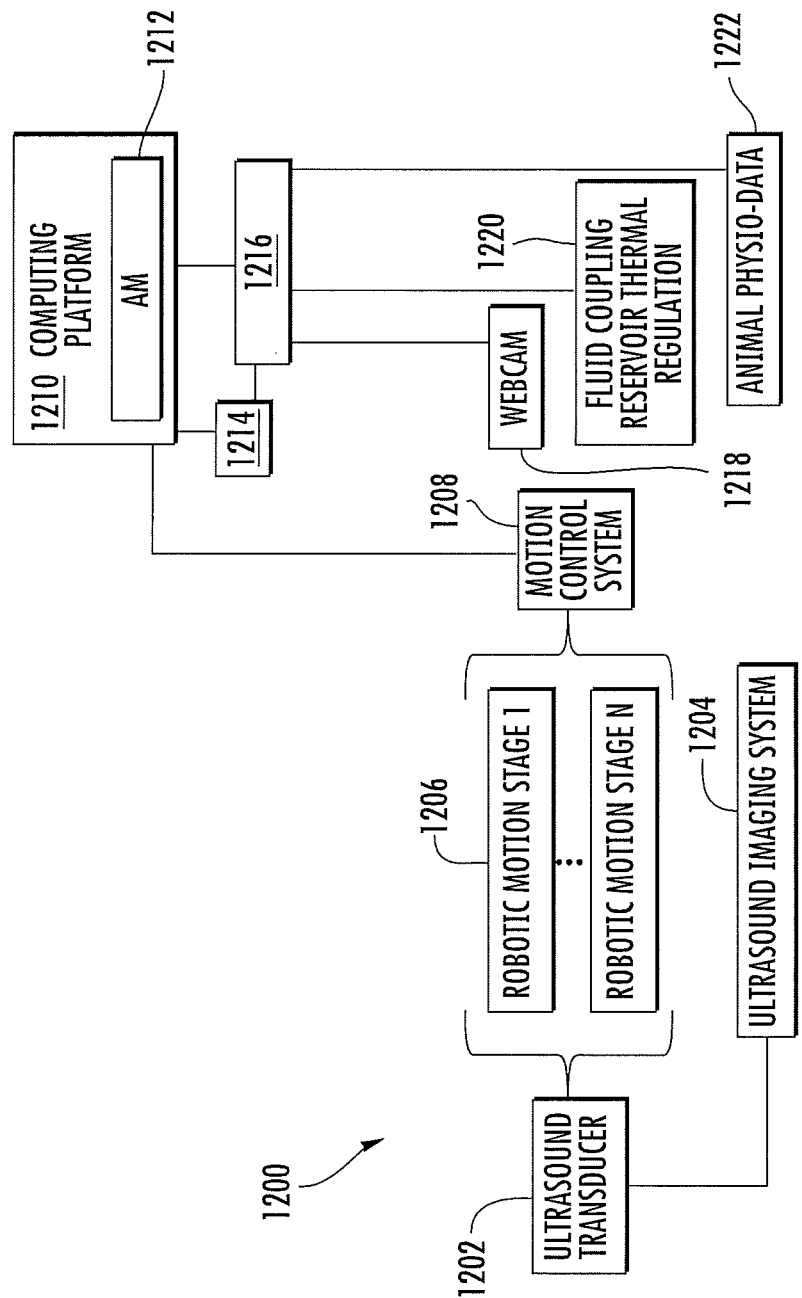
FIG. 12 is a schematic illustrating an exemplary system for preclinical ultrasound imaging of a subject according to the subject matter disclosed herein.

FIG. 12 is a schematic illustrating a system generally designated 1200 for preclinical ultrasound imaging of a subject. System 1200 may comprise an ultrasound transducer 1202, which may be an ultrasound transducer similar to transducers described herein. An ultrasound imaging system 1204 may be communicatively connected to ultrasound transducer 1202 for controlling acquisition of preclinical ultrasound images of a subject.

Transducer 1202 may be movable relative to both a subject and a reservoir or just a subject, as transducer 1202 may be coupled to the reservoir. In some aspects, transducer 1202 may be moved via one or more robotic motion stage 1206. For example, motion stage 1206 comprises two linear motion stages to independently translate transducer 1202 along an x and y axis. In another example, motion stage 1206 comprises two linear motion stages to independently translate transducer 1202 along an x and z axis and one rotational computerized stage for rotating transducer 1202 along a Θ axis. Each motion stage of the one or more robotic motion stage 1206 may be independently controllable by a motion control system, generally designated 1208, for either automatic and/or manual control by an operator.

Other entities that may be associated with system 1200 may include a reservoir for containing a coupling medium, a platform, more than one robotic stage configured to move and/or rotate the platform, a reservoir support structure, seals, membranes, one or more optical cameras, heating elements, sensors, etc., as well as any structure comprising functionality for capturing, regulating and/or storing acquired data.

In some aspects, a computing platform, generally designated 1210 may be in communication with and/or otherwise associated with motion control system 1208 and/or ultrasound imaging system 1204. In some aspects, computing platform 1210 may include functionality for configuring an apparatus to operate one or more robotic stage 1206 via motion control system 1208 (e.g., through acquisition software or by an external joystick or keypad.

Computing platform 1210 may be used for acquiring preclinical ultrasound images of a subject. Computing platform 1210 may represent any suitable entity or entities (e.g., an acquisition platform or a server farm) for acquiring preclinical ultrasound images of a subject. For example, computing platform 1210 may acquire preclinical ultrasound images associated with an apparatus, such as apparatus 300, 900, etc., using one or more ultrasound transducers.

In some aspects, computing platform 1210 may be configured to perform one or more functions associated with acquiring preclinical ultrasound images. In some embodiments, computing platform 1210 may be a stand-alone acquisition tool, an ultrasound acquisition device, or software executing on a processor. In some embodiments, computing platform 1210 may be a single node or may be distributed across multiple computing platforms or nodes.

Computing platform 1210 may include an acquisition module (AM) 1212. AM 1212 may be any suitable entity (e.g., software executing on a processor) for performing one or more aspects associated with preclinical ultrasound image acquisition and processing. AM 1212 may include functionality for acquiring preclinical ultrasound image(s) during one imaging session or multiple sessions and for processing these images. For example, AM 1212 may acquire one or more ultrasound images of a subject for processing. In this example, an AM user (e.g., a device or computing platform usable by a user or an operator) may acquire one or more preclinical ultrasound images of the subject via ultrasound imaging system 1204 associated with computing platform 1210, which may be subsequently processed by AM 1212. In addition to providing functionality for acquiring and/or processing the preclinical ultrasound images of a subject, AM 1212 may include functionality for storing the images for future use. In some embodiments, AM 1212 may include functionality for instantiating or initializing images and/or for providing the images to other computing platforms or devices. For example, AM 1212 may acquire the ultrasound images and process those images or may provide the acquired ultrasound images to other nodes to process the images.

In some aspects, AM 1212 may include or access data storage 1214 containing data and/or images related to preclinical ultrasound imaging. For example, AM 1212 may access data storage 1214 containing previous image acquisitions, mapped coordinate systems, image data, profiles, settings, or configurations. Exemplary data storage may include non-transitory computer readable media, such as flash memory, random access memory, or other storage devices. In some embodiments, data storage 1214 may be external to and/or integrated with the computing platform 1210 and/or AM 1212.

In some aspects, AM 1212 may include one or more communications interfaces 1216 for interacting with users and/or nodes. For example, AM 1212 may provide a communications interface for communicating with an AM user. In some embodiments, the AM user may be an automated system or may be controlled or controllable by a human user. The AM user may acquire and/or process the ultrasound images acquired during preclinical imaging. In some embodiments, processing the ultrasound images may include registering a currently acquired image set acquired at a second time point to a previous acquired image set acquired at a first time point.

In some aspects, the AM user may include one or more communications interfaces 1216 for interacting with one or more systems and/or devices. Such systems and/or devices may include, but are not limited to, an apparatus for acquiring preclinical ultrasound images (see, FIGS. 1A-9), an ultrasound imaging system 1204, a motion control system 1208, a video recording device (e.g., one or more webcam 1218) for capturing images regarding the positioning of the subject on the platform, thermal management system (e.g., fluid coupling reservoir thermal regulation 1220) with any sensors for regulating temperature of the coupling medium, and/or any other suitable entity or entities (e.g., storage devices containing animal physio-data 1222) implementing, acquiring, or otherwise using preclinical ultrasound images. For example, such suitable entity or entities may comprise an enterprise data storage system including multiple physical storage devices or components.

In some aspects, computing platform 1210 may include functionality for configuring an apparatus to maintain a specific offset relative to the platform during acquisition of preclinical ultrasound images. For example, where computing platform 1210 communicates with transducer 1202 via ultrasound imaging system 1204, computing platform 1210 may control movement of transducer 1202 to specified locations relative to a subject. In this example, computing platform 1210 may control movement of transducer 1202 to predetermined transducer-body offset such that transducer 1202 may be maintained and/or controlled at a predetermined (optimal) offset from a body of a subject during an imaging session, e.g., a 1-1.5 cm offset, whether a subject is moved relative to transducer 1202 or vice versa. In this example, a surface atlas of the subject may be saved to data storage 1214 that may be accessed by computing platform 1210 during the imaging session and may be utilized by computing platform 1210 to aid in maintaining the offset.

In another aspect, computing platform 1210 may include functionality to configure an ultrasound imaging system 1204 to acquire the images from positioned transducer 1202. In another aspect, computing platform 1210 may include functionality to modify conditions within the apparatus; for example, regulating temperature of a coupling medium held within a reservoir, movement of transducer 1202 to multiple spatial positions within one imaging session, etc. In some aspects, computing platform 1210 may include functionality to generate content (e.g., compounded image data using previously acquired preclinical ultrasound images) and/or retrieve stored content associated with a preclinical imaging session and may send or provide the content to other suitable entities (e.g., subject physio-data 1222 regarding the subject being imaged that has been logged in previous sessions). In some aspects, computing platform 1210 may be configured to monitor subject physiological homeostasis, including but not limited to heart rate, breathing rate, and body temperature, where this physio-data may be logged throughout an imaging study. Consequently, any physio-data logged during an imaging study may be used to retroactively gate images to remove image frames in which a subject was moving.

In some aspects, the AM user may be configured to acquire and/or process acquired ultrasound images based on existing content. For example, during preclinical image acquisition, the AM user may import transducer positioning data from a previous imaging session in order to replicate positioning of transducer 1202 in a current and/or subsequent imaging session. Consequently, computing platform 1210 may be associated with different aspects of system 1200 for acquiring preclinical ultrasound images.

In some aspects, a system for preclinical ultrasound imaging may be utilized to coarsely map (i.e., one to one spatially map) a subject's spatial position on a platform of an apparatus for preclinical ultrasound imaging in order to facilitate ultrasound imaging scan boundaries and subsequent positioning of the subject in later imaging sessions. Such a system and/or apparatus may include a system, such as system 1200, described with respect to FIG. 12, as well as any of the apparatuses described in conjunction with FIGS. 1A-9. Users of a system for preclinical ultrasound imaging may be enabled to manually and/or automatically define angular and linear regions over which to scan, how many passes to make at each location, and then execute this set of parameters. The system may update a user how much time remains for the scan. This may be achieved in one or more axes (e.g., the Z and Y axis) using one or more of the following options including but not limited to: laser-based ranging, segmentation based on webcam image feedback, pressure feedback of a subject on a platform, and/or acoustic ranging based on a priori knowledge of platform distance. Other options may also be utilized. In addition, a transducer used for acquiring the preclinical images may include a laser indicating where the transducer is currently aimed in order to allow visual feedback for the user in positioning it. This may include non-visible wavelengths which an optical detection device may detect in order to prevent reflections from endangering a user's eyes).

Mapping a subject's spatial position may be performed by acquiring an image of an organ, such as the heart, at a first time point. Location of a 2D ultrasound image acquired may be recorded in XYZ space and subsequently stored using, for example, AM 1212 of computing platform 1210. A 3D ultrasound scan showing tissue surrounding a region of interest at the first time point may then be acquired. Features of interest (e.g., organ(s), rib(s), a surface of the skin, or feature(s) that can serve as landmarks), which have at least four XYZ points associated with them, may be segmented from the 3D ultrasound scan. In some instances, four XYZ points may be the minimum number of points needed to uniquely define a coordinate system in 3D space to determine a location of the 2D ultrasound plane relative to the landmarks.

In some aspects, a spatial position of a subject at a first time point may be used to exactly position a transducer in order to acquire a 2D ultrasound image (i.e., position the scan plane) at a second time point. This may be useful in evaluating predetermined regions in a subject's body in a different imaging session. In order to use previous locations of a scan plane in XYZ space in a subsequent session, another 3D image of that subject may be acquired at a second time point. The same features of interest acquired at the first time point may be segmented out of the 3D image in order to determine a location of a 2D ultrasound plane relative to the landmarks in the second time point. The segmented landmarks may then be aligned from the data, and once this transformation is known the image data between the time points may be mapped, such that the ultrasound scan plane may be exactly positioned where the scan plane was at the first time point.

Slight adjustments may be needed for replicating positioning of a scan plane from a first time point to a second time point once image data between the time points is mapped. However, in one aspect, this may be done very precisely and iteratively by comparing two 2D images (a current image from a second time point, which updates every time a transducer is moved, compared with a previous image from a first time point, which is static) and stopping when a maximum value of correlation between the frames is reached. This may ensure more accuracy than is capable from the human eye.

In another aspect, instead of having a user define and/or segment landmarks, a whole image dataset at a second time point may be registered (manually or automatically) to an image dataset at a first time point. This may result in a same coordinate transform, as described above.

In another aspect, an optical recording device (e.g., a webcam) looking down on a subject may result in calibrated locations of XY locations. This may enable a user to come very close to an original scan plane location and/or orientation. For example, a user may add a suitable marking (e.g., fiducial landmark) to a subject's skin, one that is not likely to move very much over time, so that a location of the marking may be selected in the webcam image and transmit the transducer to that specific location.

For example and in reference to FIGS. 13A-13C, an exemplary process flow for one to one spatial mapping is illustrated, where an image set of an imaging session at a second time point is registered to an image set of either the same or different modality at a first time point. FIG. 13A illustrates a screenshot, 1300A, of a first image set at a first time point in a first coordinate system. In some aspects, the first image set may include, for example, an ultrasound image, a 2D webcam image, a 3D contour map of the animal derived by one or more webcam images, a photoacoustics image, a bioluminescence image, an x-ray image, an MRI image, a fluorescence image, a SPECT image, a PET image, an anatomical atlas, or any multimodality combination thereof. FIG. 13B illustrates a screenshot, 1300B, of a second image set at a second time point using a different coordinate system. In some aspects, the second image set may include, for example, a widefield ultrasound image volume, a 2D webcam image, or a 3D contour map of the subject derived by one or more webcam images. FIG. 13C illustrates a screenshot of the resulting registration 1300C of the image set from the second time point in FIG. 13B to the image set from the first time point in FIG. 13A, where the coordinate system between the image sets has been mapped one-to-one. Notably, once registration has been performed, a user can provide a ROI somewhere in the first image set (i.e., in FIG. 13A) that is viewable in the registered set (i.e., in FIG. 13C). Thus, the presently disclosed subject matter enables the automatic localization of one or more organ systems of interest based on the registration between image data from a first time point and a second time point.

In addition, the presently disclosed subject matter is advantageous because it enables widefield imaging of tissue volumes. More specifically, over 50% of a subject's body may be imaged, which may enable better longitudinal comparisons, thereby increasing the quality of image data. This is made possible by the system physically positioning an ultrasound transducer at different angles relative to the same tissue, and imaging the tissue without physically contacting it directly (i.e., no tissue warping). This may allow the resulting images to be rigidly registered together to ensure accurate alignment between the ultrasound image data and the secondary image data set (i.e., sampling the same tissue regions) so that measurements made within the ultrasound image data and the secondary image data set have one to one correspondence. Alignment may be performed in an automated or manual fashion, and may occur simultaneously with or subsequently to image generation.

Figure 14A:
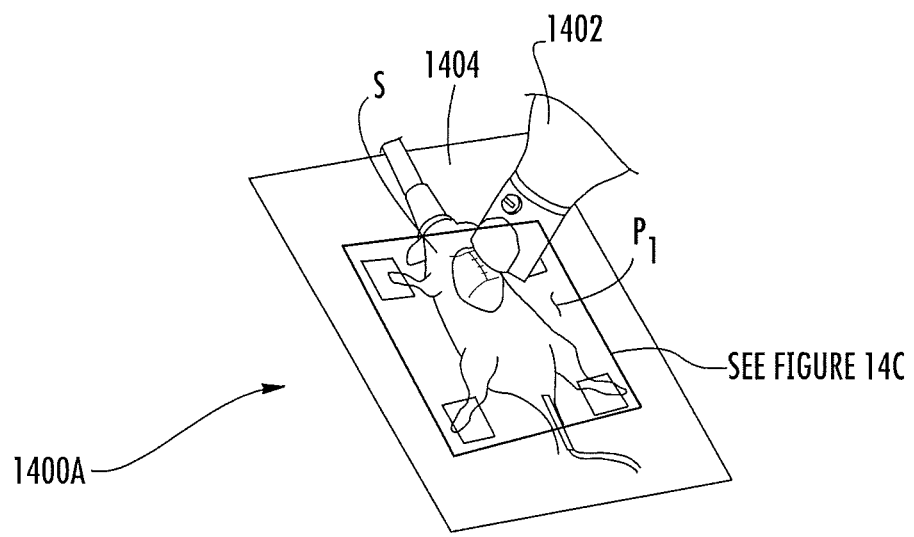
FIG. 14A is a diagram illustrating a first scan plane relative to a subject for preclinical ultrasound imaging of a subject according to the subject matter disclosed herein.
Figure 14B:
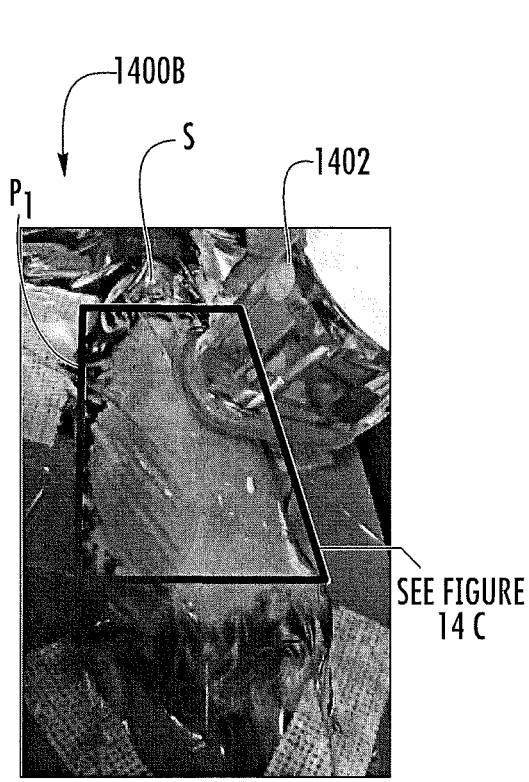
FIG. 14B is a photograph illustrating the first scan plane relative to the platform according to FIG. 14A.
Figure 14C:
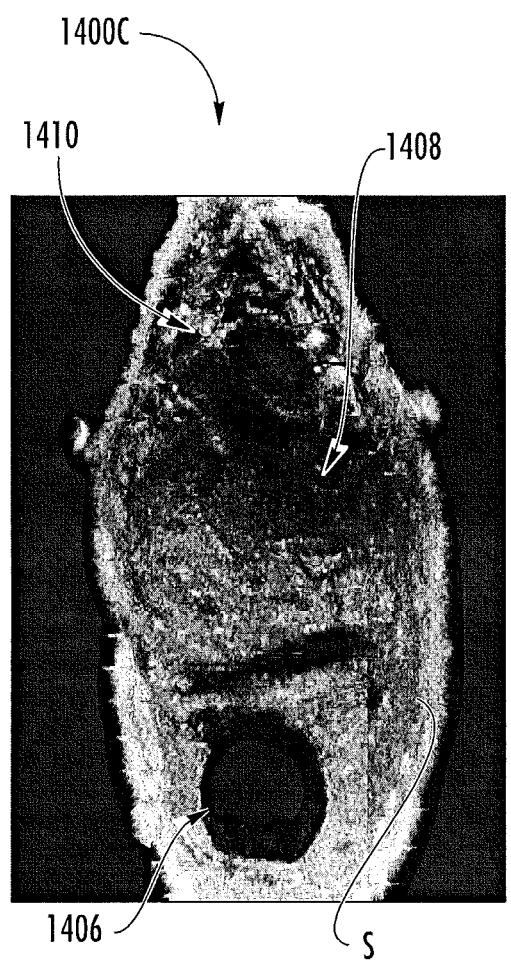
FIG. 14C is a screenshot illustrating a two-dimensional (2D) ultrasound image of the subject taken along the first scan plane according to, FIG. 14A, where a bladder, a liver, and a heart of the subject are visible.

For example, an ultrasound transducer may be positioned at three different angles relative to a same tissue (see, e.g., FIGS. 14A-C, 15A-B, and 16A-B). These angles may be +/−20 degrees and 0 degrees, with a z range of 5 cm and a z resolution of 150 μm, and 333 image frames per stack. A transducer may be positioned at more angles or less angles relative to the same tissue, as well. Referring to FIGS. 14A-C, a first angle at which an ultrasound transducer is positioned and subsequent image plane at which an ultrasound image of the subject is acquired is provided. Specifically, FIG. 14A provides a diagram of an imaging session, generally designated 1400A, of a transducer 1402 in a first spatial position relative to a subject S positioned on a platform 1404. Subject S is prepped and positioned on platform 1404 over a reservoir holding a coupling medium (not shown) in an apparatus similar to one or more apparatus described hereinabove. Transducer 1402 may be positioned in the first spatial position in either a manual or automated manner in order to scan a certain region of subject S in a first scan plane $P_1$ (e.g., a rectangular region right to left). Notably, the first spatial position of transducer 1402 may be chosen in order to image certain organs or tissues of subject S. FIG. 14B is an exemplary photograph, generally designated 1400B, of an image of transducer 1402 in the first spatial position relative to subject S as described in FIG. 14A. First scan plane $P_1$ is provided in photograph 1400B to illustrate the ROI in subject S in which transducer 1402 will acquire a 2D ultrasound image. Accordingly, FIG. 14C is an exemplary screen shot of a 2D ultrasound image, generally designated 1400C, acquired of subject S, where a bladder 1406, a liver 1408, and a heart 1410 are all visible.

Figure 15A:
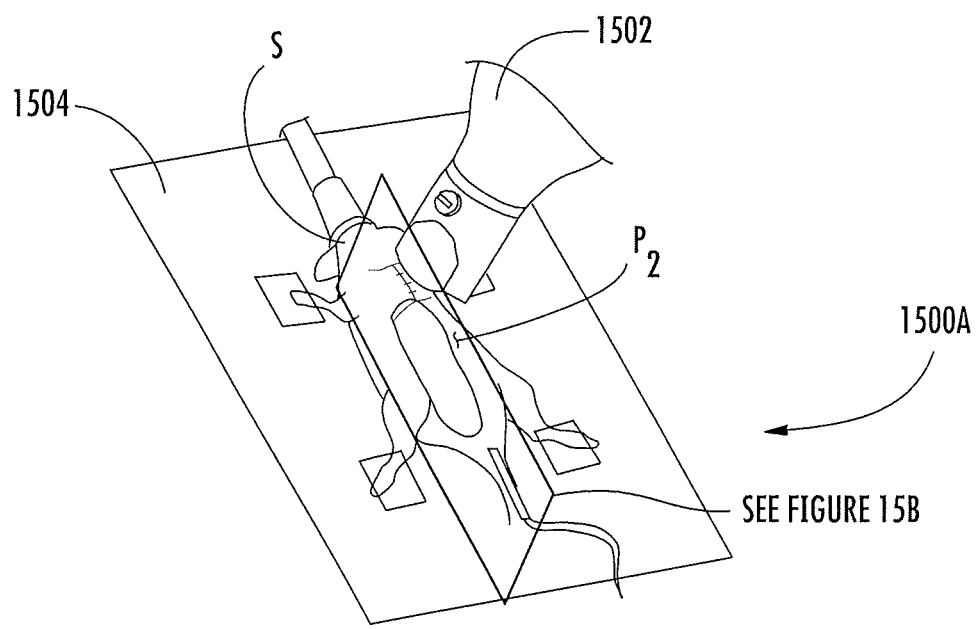
FIG. 15A is a diagram illustrating a second scan plane relative to a subject for preclinical ultrasound imaging of a subject according to the subject matter disclosed herein.
Figure 15B:
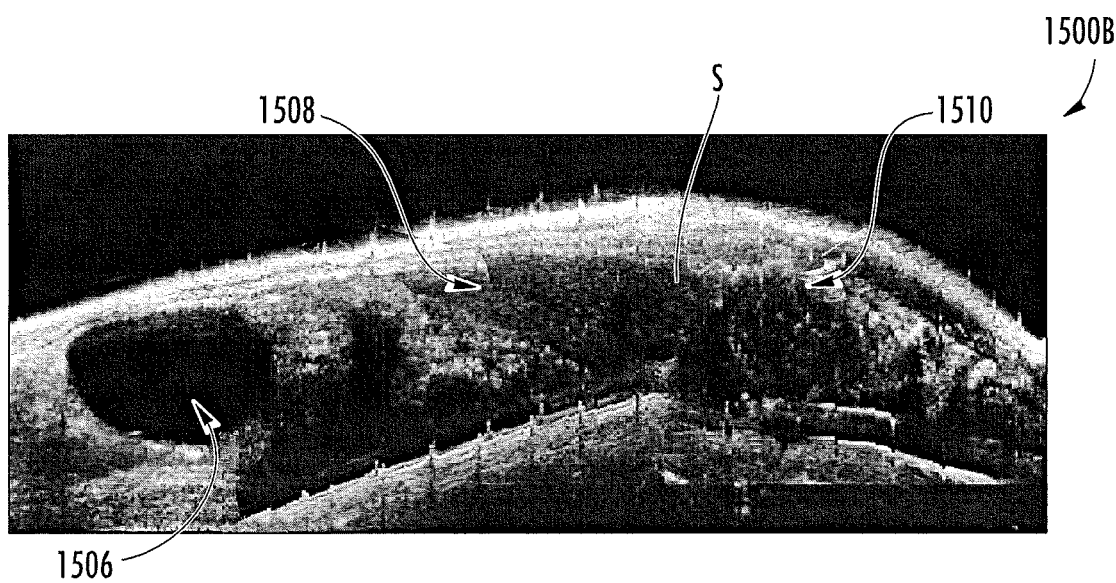
FIG. 15B is a screenshot illustrating a 2D ultrasound image of the subject taken along the second scan plane according to FIG. 15A, where a bladder, a liver, and a heart of the subject are visible.

Referring now to FIGS. 15A-15B a second angle at which an ultrasound transducer is positioned and subsequent image plane at which an ultrasound image of the subject is acquired is provided. Specifically, FIG. 15A provides a diagram of an imaging session, generally designated 1500A, of a transducer 1502 in a second spatial position relative to a subject S positioned on a platform 1504. Notably, the imaging session illustrated in FIG. 15A may be a same imaging session as that illustrated in FIG. 14A. The only difference may be that the transducer has been moved from a first spatial position to a second spatial position relative to a subject S. Transducer 1502 may be positioned in the second spatial position in either a manual or automated manner in order to scan a certain region of subject S in a second scan plane $P_2$ (e.g., a rectangular region superior to interior) in order to image the same organs or tissues from FIGS. 14A-C at a different angle. FIG. 15B is an exemplary screen shot of a 2D ultrasound image, generally designated 1500B, acquired of subject S, where a bladder 1506, a liver 1508, and a heart 1510 are all visible; albeit at a different angle than in FIG. 14C.

Figure 16A:
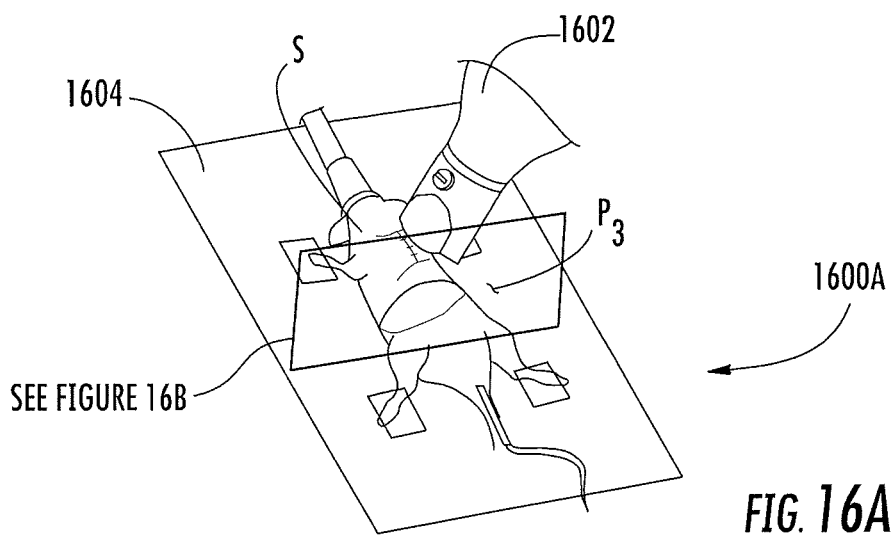
FIG. 16A is a diagram illustrating a third scan plane relative to a subject for preclinical ultrasound imaging of a subject according to the subject matter disclosed herein.
Figure 16B:
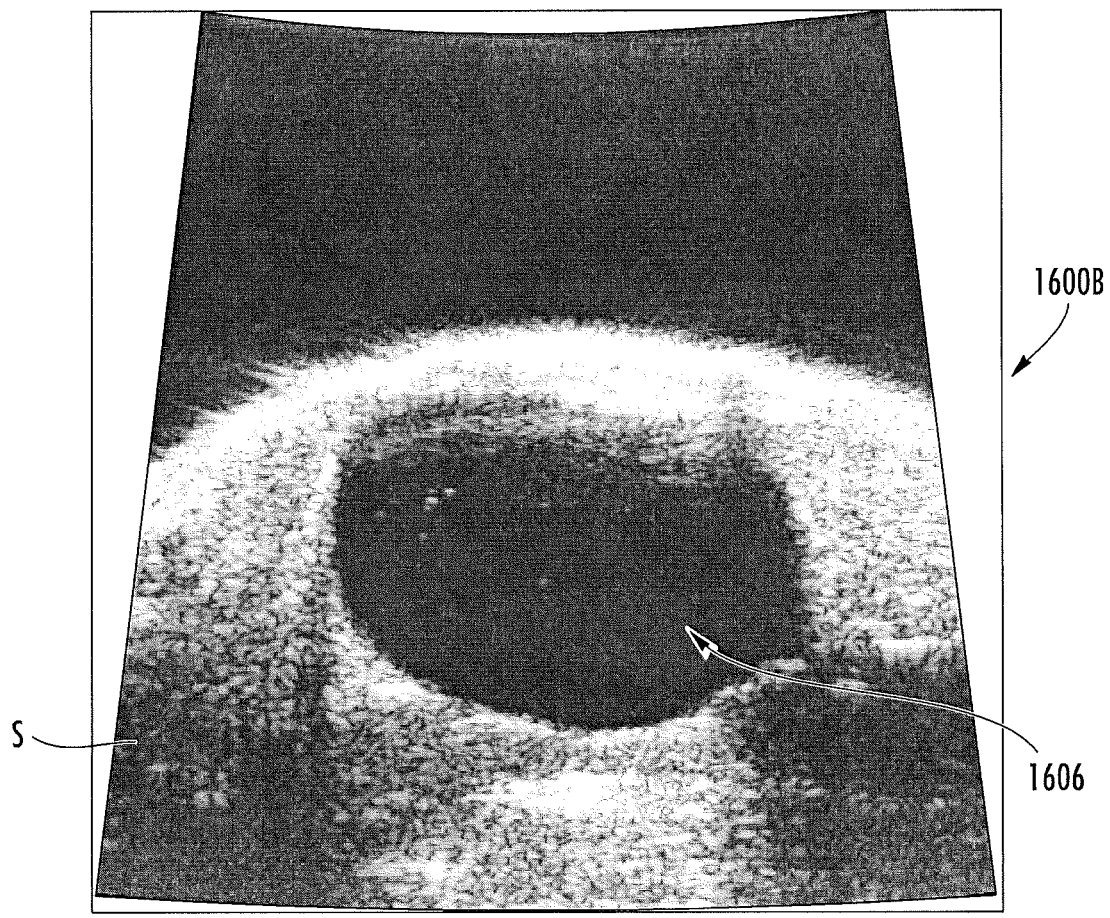
FIG. 16B is a screenshot illustrating a 2D ultrasound image of the subject taken along the third scan plane according to FIG. 16A, where a bladder of the subject is visible.

Referring now to FIGS. 16A-B, a third angle at which an ultrasound transducer is positioned and subsequent image plane at which an ultrasound image of the subject is acquired is provided. Specifically, FIG. 16A provides a schematic illustration of an imaging session, generally designated 1600A, of a transducer 1602 in a third spatial position relative to a subject S positioned on a platform 1604. Notably, the imaging session illustrated in FIG. 16A may be a same imaging session(s) as that illustrated in either one or both of FIGS. 14A and 15A. The only difference may be that the transducer has been moved from first and/or second spatial position(s) to a third spatial position relative to a subject S. Transducer 1602 may be positioned in the third spatial position in either a manual or automated manner in order to scan a certain region of subject S in a third scan plane $P_3$ (e.g., a rectangular region anterior to posterior) in order to image the same organs or tissues from FIGS. 14A-C and 15A-B at a different angle. FIG. 16B is an exemplary screen shot of a 2D ultrasound image, generally designated 16006, acquired of subject S, where only a bladder 1606, is visible; albeit at a different angle than in FIGS. 14C and 15B.

Figure 17:
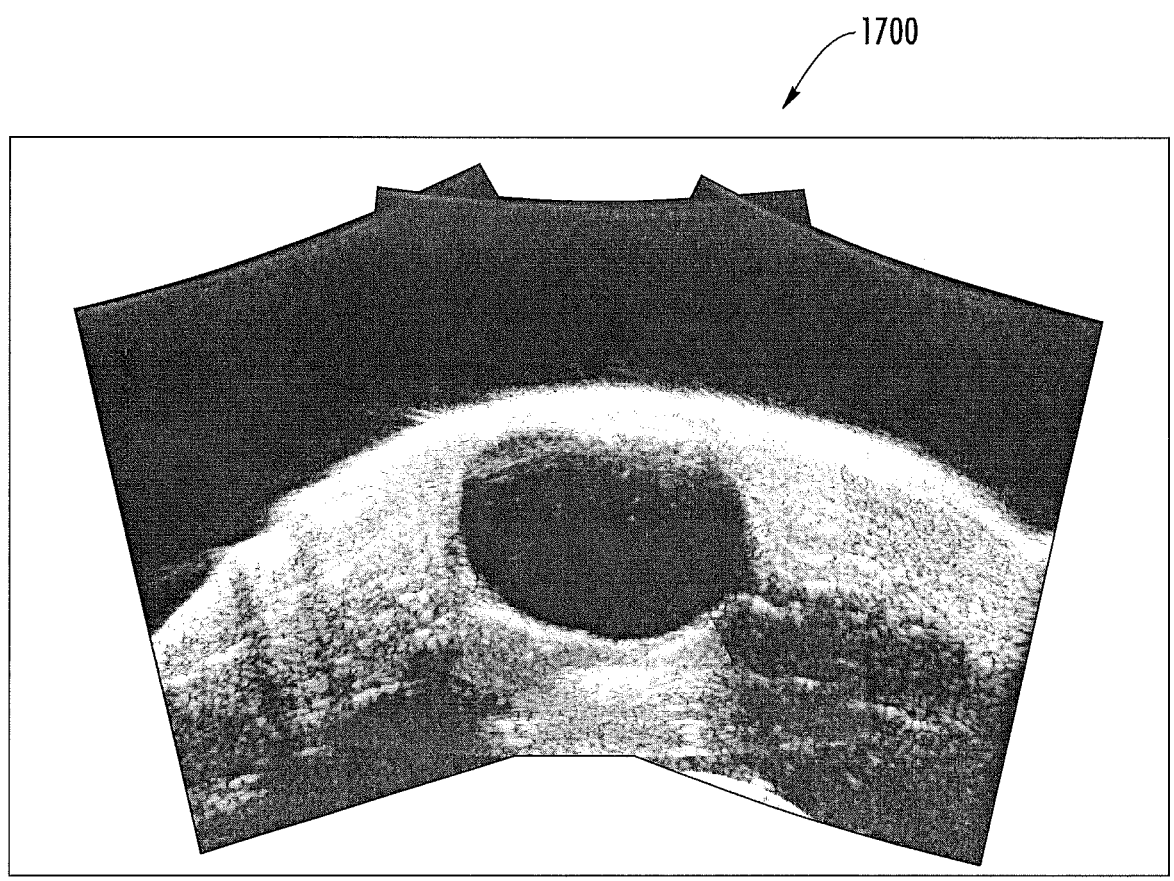
FIG. 17 is a screenshot illustrating a three-angled composite 2D ultrasound image of the bladder of the subject using the 2D ultrasound images of FIGS. 14C, 15B, and 16B.

Accordingly, once images at different reference angles of a transducer have been acquired, the images at different angles may then be compounded into a multi-angle composite image. For example, FIG. 17 is a screenshot of a three-angle composite image, generally designated 1700, of the 2D ultrasound images of the bladder acquired in FIGS. 14C, 15B, and 16B. Such a resulting composite image may have a direct and advantageous impact on a field of view (FOV), as it may be dramatically increased when compared to a single angle FOV. Such a comparison is illustrated in FIGS. 18A-B. FIG. 18A is a screenshot of a single angle 2D ultrasound image, generally designated 1800A, of a subject with a FOV having a width of $X_1$, while FIG. 18B is a screenshot of a three angle composite 2D ultrasound image, generally designated 1800B, of a same subject with a FOV having a width of $X_2$. In the example provided in screenshots 1800A and 1800B, $X_1$ is equal to approximately 1.8 cm, while $X_2$ is equal to approximately 3.7 cm. Thus, the single acquisition image in FIG. 18A has a FOV that is approximately two times less than the FOV of the three angle composition image of FIG. 18B, such that compounding multiple images acquired of a subject from different angles into a single image may provide a larger FOV for analysis and study.

In addition, the apparatuses, systems, and methods described herein enable users to specify a desired signal to noise ratio (SNR) in their final image. This may achieved by computing how many angular projections would be acquired to result in the specified SNR, and then automatically determining the angular range over which to acquire the data, and displaying the required time for the user. In some aspects, the system may enable the user to specify a desired acquisition time, and then SNR is maximized given the time constraint and spatial area being scanned.

The apparatuses, systems, and/or methods according to the present subject matter may also include functionality for producing values for cardiac function, such as, for example, left ventricular (LV) wall thicknesses—proximal and distal, LV chamber dimensions at systole and diastole, fractional shortening, ejection fraction, heart rate, and cardiac output. Traditionally, capturing values for cardiac function has proven difficult using conventional imaging techniques. This is because of the technical challenge in placing a sampling line or plane in exactly the same position within the body between subjects or time points, leading to increased variance. Additionally, data samples of the heart can be corrupted by the ribs, respiratory motion, and other reasons. However, the following presents an advantageous approach that reduces time, cost, and the effect of inter-user variability.

Specifically, an amount of time that a user has to actively interact with the apparatus and/or system may be reduced by the subject matter described herein. By positioning, a raster scan grid approximately near the heart (e.g., as indicated by a laser or light to show the user where the scan will be), the user may configure the apparatus and/or system, actuate the apparatus and/or system, and let the apparatus and/or system collect data, without the need for continual supervision by the user. During the time that the apparatus and/or system may be automatically acquiring data, the user may be able to prepare the next subject, thereby increasing the efficiency of the workflow. In addition, the effect of inter-user variability is reduced because the user may not have control over the placement of the scan plane, since movement of the linear and/or rotational stages (which position the transducer) of the apparatus and/or system may be controllable automatically by a computing platform associated with the apparatus and/or system.

Moreover, reducing the overall cost of the technology may be enabled by using a single ultrasound transducer (or small number of ultrasound transducers) and moving the single transducer around using the above-described apparatus, compared to a conventional ultrasound probes which attempt to produce 2D or 3D images for user interface. Such "image-producing" transducer arrays significantly increase the price of heart-analysis tools, while the apparatus or system according to the present subject matter collects individual lines of data about how the heart walls are moving in different areas of the organ and then interpolates between those lines to create a model of the heart beating in 3D. Although, the apparatus or system of the present subject matter could be used to create a 2D image of the heart, it may be relatively slow (several seconds per image due to the necessity that the transducer be physically translated along the subject).

As mentioned above, the system and/or apparatus used to produce values for cardiac function may be an m-mode line, pulse wave Doppler, or tissue Doppler, and/or any other mode of ultrasound which acquires a 1D spatial sampling region over time. Illustrated below is an exemplary workflow for raster scanning and acquiring data of a subject using an apparatus and/or system of the type described above.

Figure 19:
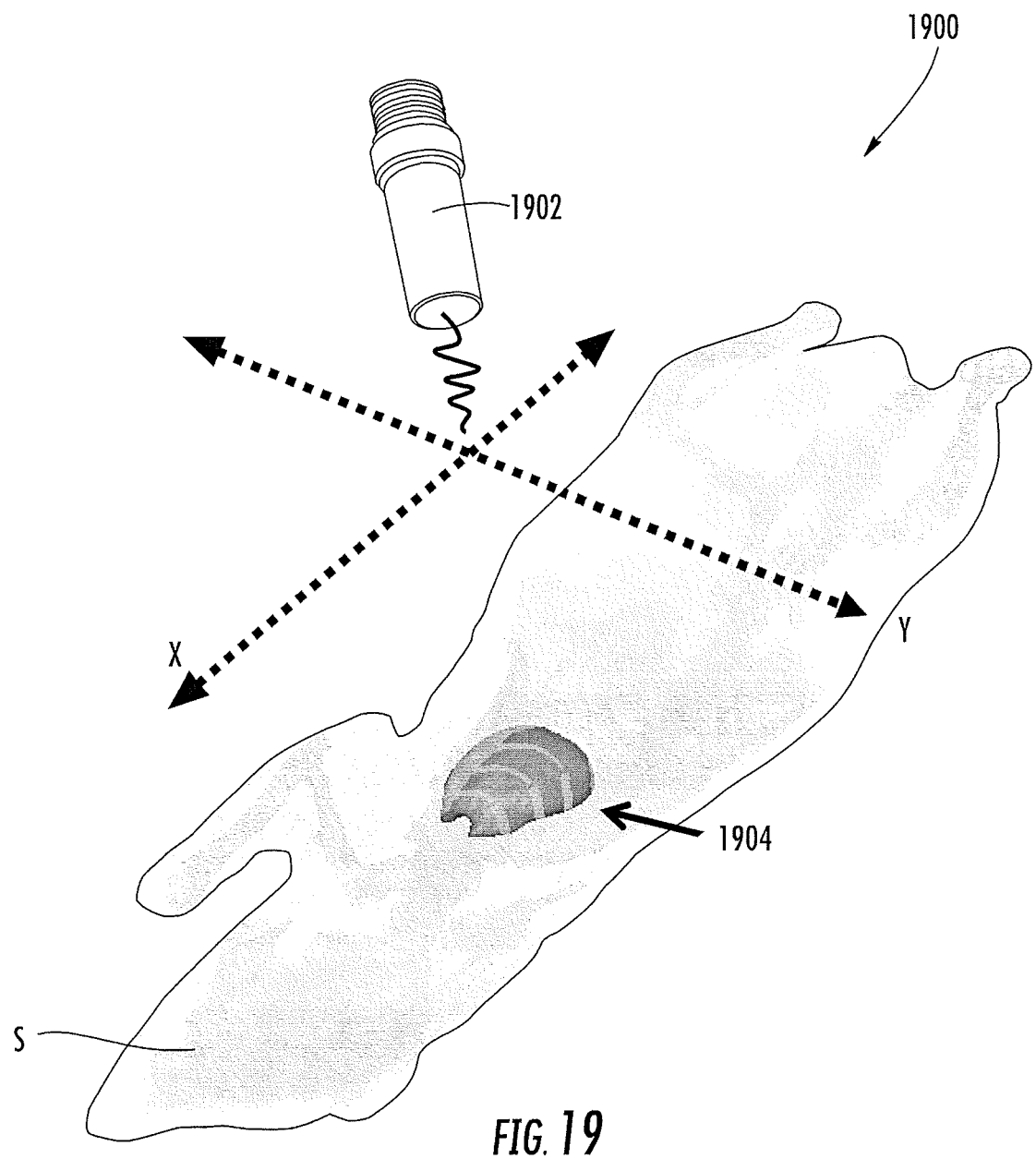
FIG. 19 is a computer generated image illustrating at least one exemplary ultrasound transducer raster scanning a subject according to the subject matter disclosed herein.

FIGS. 19-23B each illustrates a process for producing values for cardiac function as described above. Referring now to FIG. 19, a computer generated image of an exemplary setup, generally designated 1900, is provided where a transducer 1902 (e.g., a 30 MHz piston) may be aligned to an approximate location on a subject S. For example, transducer 1902 may be aligned to an approximate location on subject's chest where heart 1904 is expected to be. Transducer 1902 may be translated over heart 1904 along x and y axes using one or more motion stages coupled to transducer 1902.

Figures 20A, 20B:
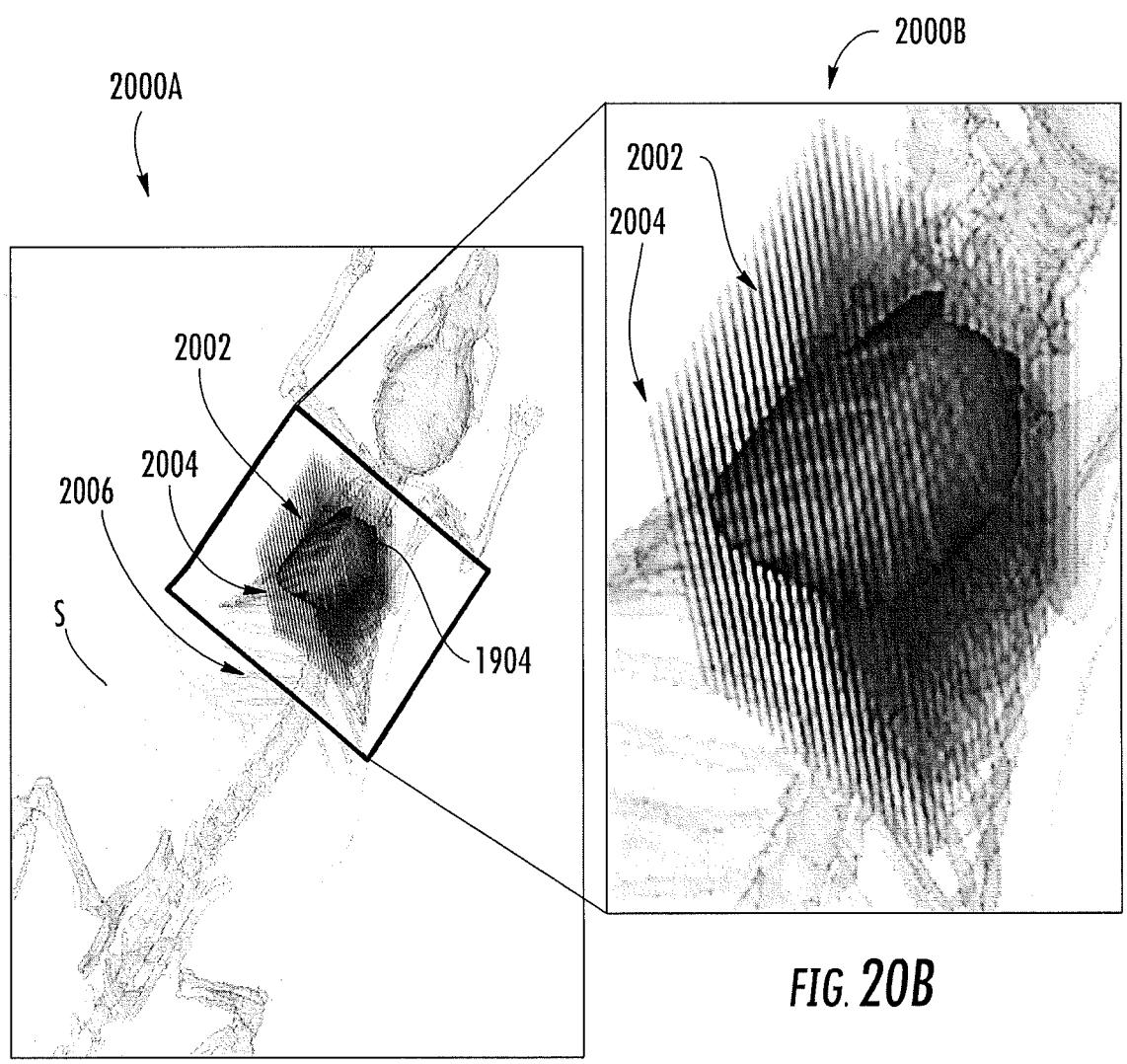
FIG. 20A is a computer generated image illustrating an exemplary raster scan grid over a subject according to the subject matter disclosed herein.
FIG. 20B is a computer generated image illustrating a detailed view of the raster scan grid of FIG. 20A.

FIG. 20A is a computer generated image, generally designated 2000A, illustrating a subject S with an exemplary sampling grid 2002 provided thereon. Further to FIG. 19, sampling may be performed in an XY grid 2002 in the approximate location of where heart 1904 is expected to be on a chest of subject S. This may be estimated or it may be more precisely determined using, for example, lasers to indicate where the ultrasound grid will appear on a chest of subject S. Additionally, an even more precise approach of determining where heart 1904 may be comprises acquiring a picture of subject S (e.g., in the prone position while the subject is on a platform, registering the image to an "atlas", which is able to detail where the heart is located in a subject when it is positioned in the current manner photographed, etc). Additionally, a 3D ultrasound volume, or "scout scan" may be used to localize the boundaries of the desired organ or tissue, and positioning of the raster grid.

Once the approximate area of heart 1904 is determined, a motion stage (not shown) may move transducer 1902 to a center of grid 2002, and then move it iteratively through a plurality of XY locations across a chest of subject S at predetermined spacings (e.g., 0.05 mm-1 mm), over a predetermined grid size (e.g., 0.5 cm-2 cm) and for a predetermined amount of time at each location (e.g., 0.5-5 seconds). Thus, grid 2002 is composed of a plurality of 1D ultrasound lines 2004, which may be collected at a predetermined line-sampling rate (e.g., 100 Hz-5,000 Hz) and stored in memory. For example, there may be 400 total sample lines 2004 in a grid 2002, although this number may be larger or smaller depending on a size of grid 2002. FIG. 20B is a computer generated image, generally designated 2000B, including a detailed view of grid 2002 having a plurality of sampling lines 2004. Notably, although some of sampling lines 2004 may be corrupted by ribs 2006 of subject S, these may be automatically removed from the dataset (see FIG. 20A). In order to achieve enough data samples at each location (e.g., 4 heart beats) a total time for a grid 2002 may be approximately between three and four minutes; preferably 3 minutes and 35 seconds. However, it is noted that less data samples may require less time for the grid and larger data samples may require more time for the grid.

While the 1D ultrasound data is being collected, electrocardiogram (ECG) data of a subject's heartbeat may also be collected by any computing platform and/or nodes (e.g., computing platform 1210, FIG. 12). Any respiration-induced motion may be removed after acquisition using passive gating, or another technique. For example, passive gating may be accomplished by determining if a cross correlation function has a strong frequency component at the rate at which a normal subject breathes (e.g., less than 1 Hz, where a mouse heart is usually around 8 Hz). Once data has been acquired, it may be determined which lines of data correspond to valid data captured from the heart. This may be done by determining a cross correlation function between lines of data at each location, and creating a scoring system which increases a location's score if the cross correlation function at given location has the same frequency and phase as the ECG signal recording the heart's motion. In other words, if the ECG signal says the heart should be beating, and the ultrasound data shows something happening at the same exact point in time, that's a strong indicator that the location is on the heart. For example, in FIGS. 20A-B, the acquired 1D ultrasound image (i.e., lines 2004) may be considered valid data because they were taken from a location on heart 1904, rather than a location that was not on heart 1904 of subject S.

Using valid data (i.e., data that is indicative that a scan location is on the heart (or on a desired organ)), relevant walls of heart 1904 may be segmented or "localized" in each m-mode trace line. A screenshot of the acquired 1D ultrasound image, generally designated 2100A, of a portion of lines 2004, is illustrated in FIG. 14, where there are four clear trace lines 2102A-2108A. Depending on an angle of the ultrasound beam, screenshot 2100A may be representative of a right ventricle wall (posterior or anterior), left ventricle wall (posterior or anterior), or a septum, among other surfaces or interfaces in heart 1904 of subject S.

Segmentation of trace lines 2102A-2108A may be accomplished either manually or in an automated manner. For example, FIG. 21B provides a set of line drawings, generally designated 2100B, where each line drawing is an automated segmentation 2102B-2108B that corresponds to the curvature of one of the four surfaces extracted from each m-mode line 2102A-2108A in FIG. 21A. For example, automated segment 2102B corresponds to m-mode line 2102A, automated segment 2104B corresponds to m-mode line 2104A, automated segment 2106B corresponds to m-mode line 2106A, and automated segment 2108B corresponds to m-mode line 2108A.

Figure 21A:
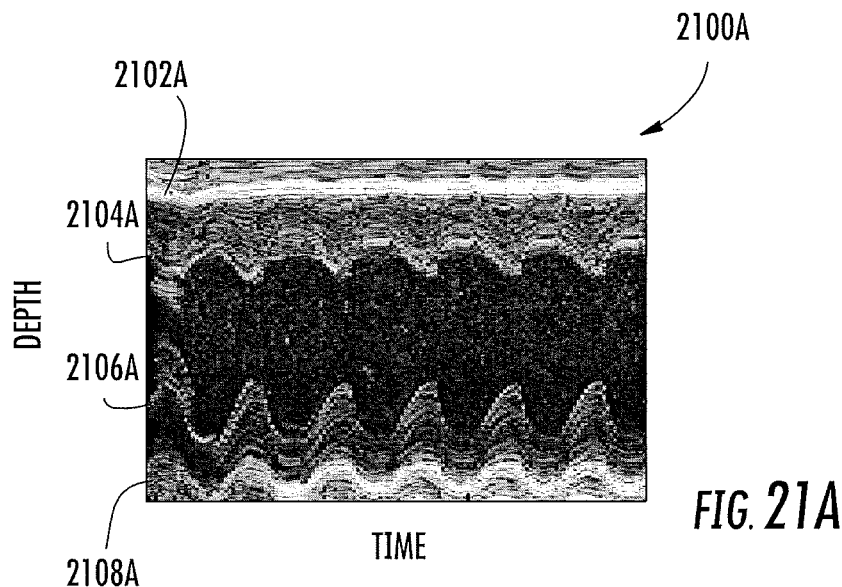
FIG. 21A is a screenshot illustrating an exemplary m-mode trace line from the raster scan grid of FIG. 20B according to the subject matter disclosed herein.
Figure 21B:
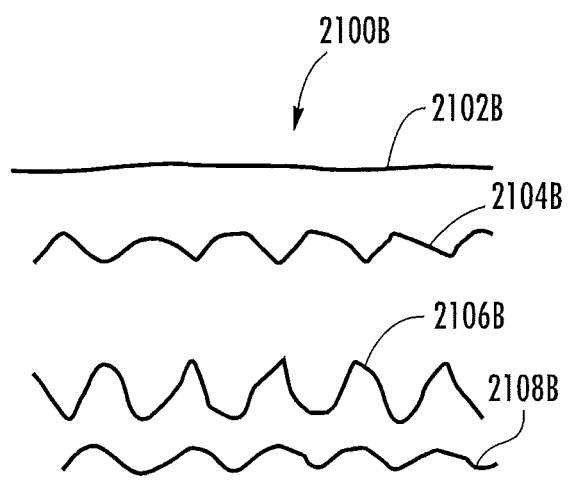
FIG. 21B is a set of line drawing illustrating automated segmentations from four surfaces extracted from the screenshot of the m-mode trace line of FIG. 21A.
Figure 22:
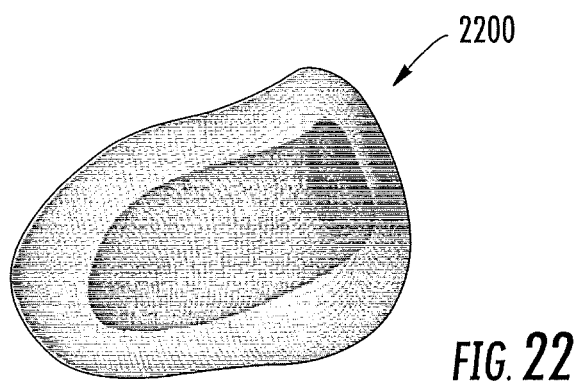
FIG. 22 is a 3D model illustrating an exemplary 3D mesh built from at least a portion of the automated segmentations of FIG. 21B.

Accordingly, a sparsely sampled grid of heart wall locations at all times during the cardiac cycle may be modeled by fit to the sparse-spatial/high-temporal sampled segmentations of each m-mode trace line (see, e.g., FIGS. 21A-B). For example, FIG. 22 illustrates a 3D model of a heart, generally designated 2200, fit to sparse-spatial/high-temporal sampled segmentations. Notably, by interpolating between these points at each time step through the cardiac cycle, a 3D mesh of the relevant surfaces of the heart (the epicardium and endocardium walls, for example) may be built up. This interpolation may be done very simply using a spline based approach, although it may also be done using a more complex image-to-atlas registration approach, where movement of the heart is watched and attempted to be aligned with how a heart normally moves during the cardiac cycle. The 3D mesh may be refined and corrected. In addition, several quantitative outputs may be determined from the model of the heart, such as: LV wall thicknesses (proximal and distal), LV chamber dimensions (systole and diastole), fractional shortening, ejection fraction, heart rate, and/or cardiac output. However, strain calculations and Doppler of flow or tissue may not be determined from the fitted heart model.

Figure 23A:
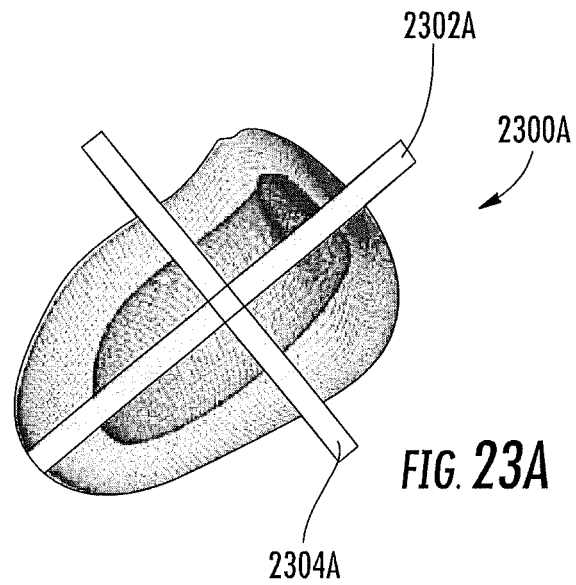
FIG. 23A is a 3D model of FIG. 22 illustrating optimal long and short axes.

Once the 3D mesh of the heart is obtained, optimal long and short axes positions/orientations of the subject's heart may be determined using the 3D model. In FIG. 23A, a 3D model, generally designated 2300A, of the heart 1904 of subject S with optimal long 2302A and short axes 2304A indicate the short axis end systole, short axis end diastole, long axis end systole, and long axis end diastole. Using optimal long 2302A and short 2304A axes modeled on the 3D model 2300A, 2D scan plans may be defined in order to acquire b-mode images. The b-mode images may be acquired by translating the 1D sampling lines along a predetermined trajectory to build up a 2D image by slowly translating the beam laterally through tissue of the subject. Translation of the beam may be accomplished through several cardiac cycles in order to acquire a video of the heart beating.

Figure 23B:
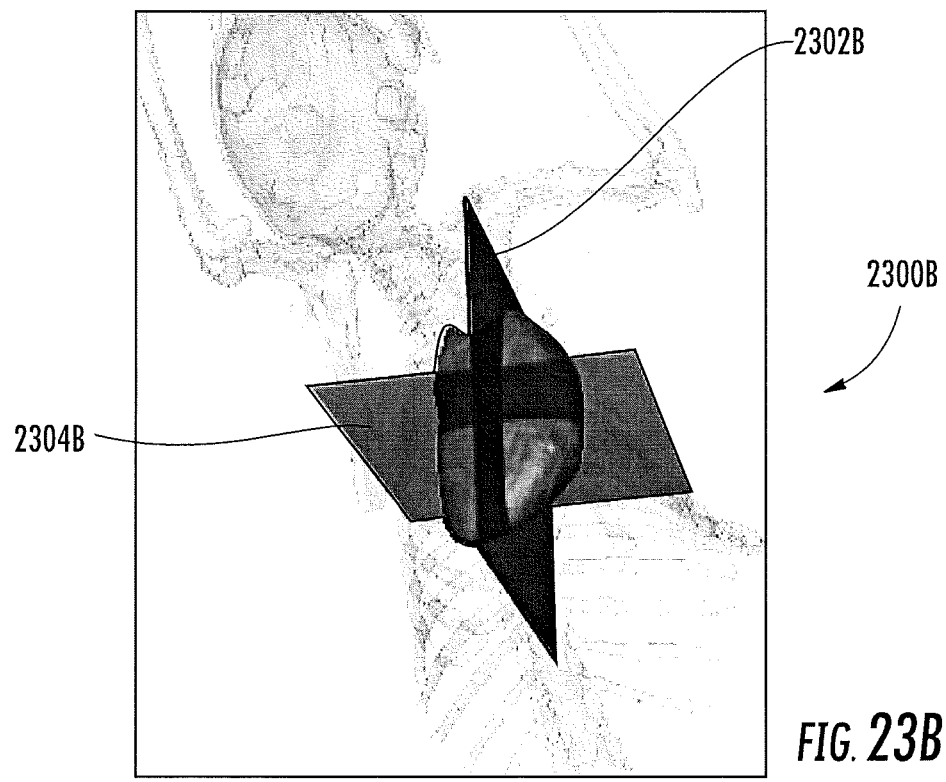
FIG. 23B is a computer generated image of the subject in FIG. 19 illustrating 2D scan planes about the heart of the subject.

In some aspects, the scan planes may be manually defined and selected, or may be automated once a model of the heart is created. As illustrated in FIG. 23B, a computer generated image illustrating the location of the heart on the subject, generally designated 2300B is provided, where the 3D model of the heart 2300A is used to define 2D scan planes 2302B and 2304B.

Figure 24:
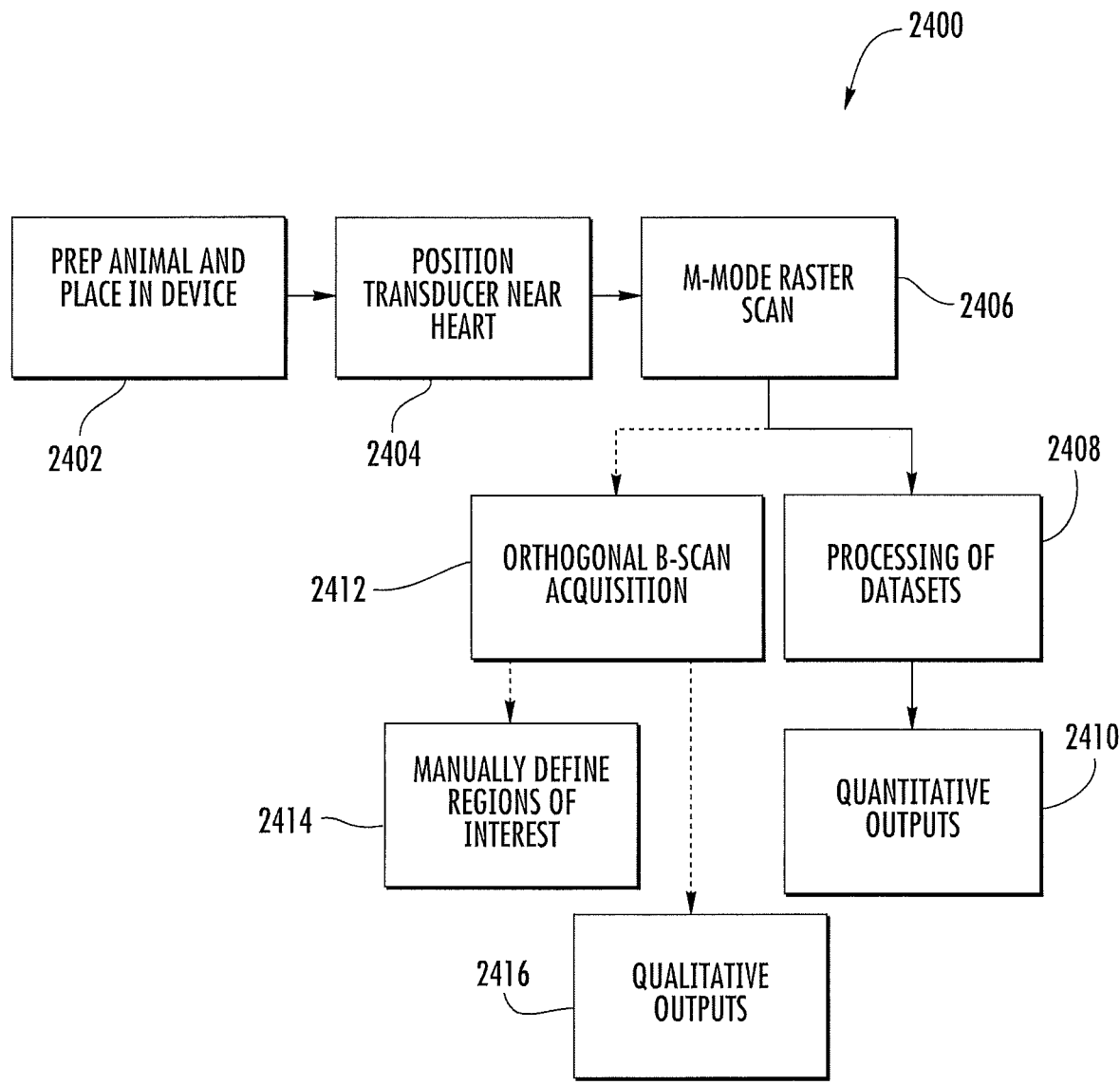
FIG. 24 is a process flow diagram illustrating a method for raster scanning a subject according to the subject matter disclosed herein.

Consequently, producing values for cardiac function for one subject may be accomplished in approximately less than 13 minutes and 30 seconds. FIG. 24 is an example flow chart, generally designated 2400, for such a process. In comparison, conventional workflows for producing values for cardiac function, which include raster scanning and acquiring data, have taken as long as 28 minutes for one subject. Exemplary flow chart 2400 illustrates a first step 2402, during which time subject prep and positioning may occur. For example, a subject may be prepared and placed in an apparatus, for example a SonoVol device, used for preclinical ultrasound imaging in approximately five minutes. Five minutes may be a typical preparation and positioning time for a subject in a study.

In a second step 2404, a transducer may be positioned near a region of interest over the subject. For example, a transducer may be positioned over a heart in approximately thirty seconds to one minute. Such a range of time, i.e., thirty seconds to one minute, may be a dramatic decrease in positioning in time compared to typical positioning times which may be up to approximately five minutes.

In a third step 2406, an m-mode raster scan may be performed over a region of interest of the subject. For example, a raster scan grid in x-y axes may be performed in approximately three minutes and thirty seconds. Typical raster scan times may be approximately five minutes.

In a fourth step 2408, datasets may be processed. For example, data obtained from the m-mode raster scan may be processed in approximately less than one minute. Advantageously, this is where the most significant time savings in producing values for cardiac functions may be achieved as typically dataset processing may take up to thirteen minutes per imaging session per subject.

In a fifth step 2410, quantitative outputs may be transmitted. For example, any analysis of the datasets from the fourth step 2408 may be transmitted and saved to a database (e.g., database 1214, FIG. 12).

In an optional step 2412, an orthogonal b-scan may be acquired. For example, a high resolution b-scan image may comprise a lateral FOV of approximately 1.5 cm with a lateral resolution of 120 µm and an acquisition time of approximately one minute and thirty seconds. Alternatively, prior to acquiring the b-mode images, another round of data in addition to step 2406, may be collected having a finer sampling density over the area where it has been validly determined that the heart is located on the subject. Doing so may further increase the accuracy of determining the location of the subject's heart.

In an optional step 2414, manual definition of one or more ROI may be performed. For example, an operator may define one or more ROI in approximately two minutes.

After step 2412, in step 2416, qualitative outputs based on the b-scan image acquired may be transmitted and saved to a database (e.g., database 1214, FIG. 12).

Accordingly, a preclinical ultrasound imaging session for a single subject may be dramatically reduced to approximately ten minutes in comparison to typical sessions which may take approximately twenty eight minutes. Reduction of subject preparation time may be further reduced in order to further reduce workflow time. For example, anesthesia induction/subject preparation may be accomplished while the apparatus and/or system described above is raster-scanning and acquiring data, which may reduce the time for each imaging session by three to four minutes, thereby resulting in completion of an entire days worth of work using conventional methods to less than three hours.

Figure 25:
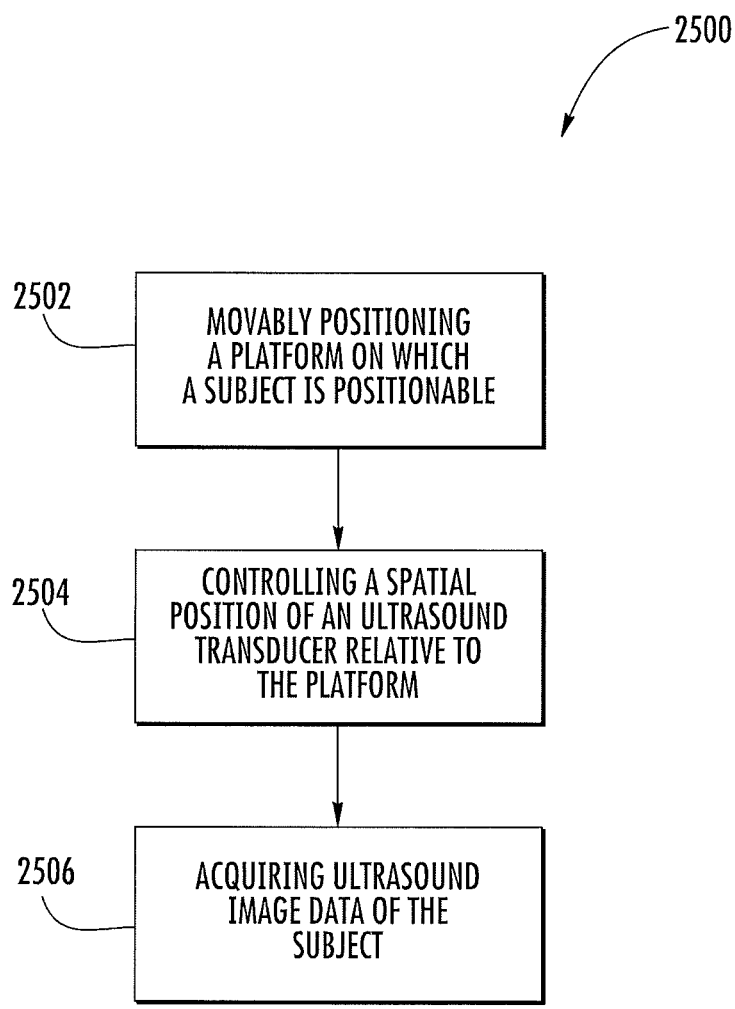
FIG. 25 is a process flow diagram illustrating a method for preclinical ultrasound imaging of a subject according to the subject matter disclosed herein.

Referring now to FIG. 25, a process flow diagram, generally designated 2500, for preclinical ultrasound imaging of a subject is provided. In a first step, 2502, a platform, on which a subject is positionable is movably positioned. For example, a subject S may be movably positioned on a platform (e.g., 808, FIG. 8).

In a second step, 2504, a spatial position of at least one ultrasound transducer relative to the platform may be controlled by at least one motion stage. For example, a spatial position of an ultrasound transducer 402 relative to a subject S may be controlled by two linear stages, an x-axis motion stage 504 and a y-axis motion stage 506 (FIG. 5). In other examples, a spatial position of an ultrasound transducer 302 relative to a subject S may be controlled by two linear stages, a y-axis stage 306 and a z-axis stage 308 and a rotational stage, a Θ-axis stage 310 (FIG. 3).

In a third step, 2506, ultrasound image data of the subject may be acquired. For example, ultrasound image data of a subject may be acquired and transmitted to a computing platform for data processing and/or analysis.

It will be understood that various details of the subject matter described herein may be changed without departing from the scope of the subject matter described herein. Furthermore, the foregoing description is for the purpose of illustration only, and not for the purpose of limitation.

What is claimed is:

1. An apparatus for preclinical ultrasound imaging of a preclinical subject, the apparatus comprising:

a platform including an aperture and an acoustic coupling medium impermeable membrane on which a preclinical subject is positionable, the platform supporting the preclinical subject from beneath the preclinical subject, wherein the preclinical subject comprises a small animal;

a reservoir located beneath the platform and containing an acoustic coupling medium;

wherein the acoustic coupling medium impermeable membrane is sealed to the platform via a rigid frame and covers the aperture to prevent the small animal from being submerged in the acoustic coupling medium;

at least one ultrasound transducer located beneath the platform within the acoustic coupling medium for movably scanning the small animal from beneath the platform and from within the acoustic coupling medium; and at least two motion stages for controlling a spatial position of the least one ultrasound transducer relative to the small animal in order to acquire ultrasound image data of the small animal, wherein the at least two motion stages include a first motion stage for moving the at least one ultrasound transducer in a first direction along a first axis and a second motion stage for moving the at least one ultrasound transducer in a second direction that is non-parallel to the first direction, the at least two motion stages are not components of the at least one ultrasound transducer, the at least two motion stages are configured to move the at least one ultrasound transducer in a pattern in which the at least one ultrasound transducer is scanned along parallel coplanar lines in the first direction that are spaced from each other in the second direction, and the second direction is perpendicular to the first direction, wherein the at least two motion stages are movable to allow generation of a three-dimensional (3D) volume ultrasound image of the small animal.

2. The apparatus of claim 1, further comprising an ultrasound imaging system, wherein the at least one ultrasound transducer is associated with the ultrasound imaging system.

3. The apparatus of claim 1, wherein the at least two motion stages are configured to move the at least one ultrasound transducer into at least a first spatial position and at least a second spatial position to acquire ultrasound image data of the small animal at each spatial position.

4. The apparatus of claim 1, further comprising a computing platform associated with the apparatus and configured to register the ultrasound image data to a secondary image data set, of either a same or a different modality from the ultrasound image data in order to ensure accurate alignment between the ultrasound image data and the secondary image data set so that measurements made within the ultrasound image data and the secondary image data set have one to one correspondence.

5. The apparatus of claim 1, further wherein the reservoir is movable in relation to the platform.

6. The apparatus of claim 5, wherein the at least one ultrasound transducer is coupled to a bottom surface of the reservoir, such that the reservoir and the at least one ultrasound transducer are configured to move relative to the platform on which the small animal is positionable.

7. The apparatus of claim 5, wherein the at least one ultrasound transducer is configured to translate substantially either above and/or below the platform on which the small animal is positionable.

8. The apparatus of claim 5, wherein the reservoir comprises a tank and the acoustic coupling medium impermeable membrane creates a seal between the small animal and the acoustic coupling medium, or the reservoir comprises a bag creating a seal between the small animal and the acoustic coupling medium in order to provide contact-free imaging between the at least one ultrasound transducer and the small animal.

9. The apparatus of claim 1, further comprising a motion control system configured to independently control motion of each of the at least two motion stages.

10. The apparatus of claim 1, wherein the platform comprises fiducial landmarks for enabling registration of the ultrasound image data to at least one functional imaging modality.

11. The apparatus of claim 10, wherein the at least one functional imaging modality comprises at least one modality selected from the group consisting of: bioluminescence, fluorescence, cryoimaging, single-photon emission computerized tomography (SPECT), and positron emission tomography (PET).

12. The apparatus of claim 1, wherein the at least two motion stages are movable to allow generation of a full body three-dimensional (3D) volume ultrasound image of the small animal.

13. A method for preclinical ultrasound imaging of a preclinical subject, the method comprising:
movably positioning a platform including an aperture and an acoustic coupling medium impermeable membrane on which a preclinical subject is positionable, the platform supporting the preclinical subject from beneath the preclinical subject, wherein the preclinical subject comprises a small animal;
providing a reservoir located beneath the platform and containing an acoustic coupling medium;
wherein the acoustic coupling medium impermeable membrane is sealed to the platform via a rigid frame and covers the aperture to prevent the small animal from being submerged in the acoustic coupling medium;
locating at least one ultrasound transducer beneath the platform and in the coupling medium for movably scanning the preclinical small animal from beneath the platform and from within the acoustic coupling medium;
controlling, by at least two motion stages, a spatial position of the at least one ultrasound transducer relative to the platform; and
acquiring ultrasound image data of the small animal, wherein the at least two motion stages include a first motion stage for moving the at least one ultrasound transducer in a first direction along a first axis and a second motion stage for moving the at least one ultrasound transducer in a second direction that is non-parallel to the first direction and the at least two motion stages are not components of the at least one ultrasound transducer, the at least two motion stages are configured to move the at least one ultrasound transducer in a pattern in which the at least one ultrasound transducer is scanned along parallel coplanar lines in the first direction that are spaced from each other in the second direction and the second direction is perpendicular to the first direction, wherein the at least two motion stages are movable to allow generation of a three-dimensional (3D) volume ultrasound image of the small.

14. A system for preclinical ultrasound raster scanning of at least one organ or tissue in a preclinical subject, the system comprising:
at least one ultrasound imaging system;
at least one ultrasound transducer associated with the at least one ultrasound imaging system and positionable relative to a preclinical subject, wherein the preclinical subject comprises a small animal;
an apparatus comprising:
a platform including an aperture and an acoustic coupling medium impermeable membrane on which the preclinical subject small animal is positionable, the platform supporting the small animal from beneath the small animal;
a reservoir located beneath the platform and containing an acoustic coupling medium;
wherein the acoustic coupling medium impermeable membrane is sealed to the platform via a rigid frame and covers the aperture to prevent the small animal from being submerged in the acoustic coupling medium;
wherein the at least one ultrasound transducer is located beneath the platform and in the acoustic coupling medium for movably scanning the small animal from beneath the platform and from within the acoustic coupling medium; and
at least two motion stages for controlling a spatial position of the at least one ultrasound transducer relative to the platform in order to acquire ultrasound image data of the small animal, wherein the at least two motion stages include a first motion stage for moving the at least one ultrasound transducer in a first direction along a first axis and a second motion stage for moving the at least one ultrasound transducer in a second direction that is non-parallel to the first direction and the at least two motion stages are not components of at least one ultrasound transducer, the at least two motion stages are configured to move the at least one ultrasound transducer in a pattern in which the at least one ultrasound transducer is scanned along parallel coplanar lines in the first direction that are spaced from each other in the second direction and the second direction is perpendicular to the first direction; and
a computing platform having a hardware processor and a memory and being associated with the at least one ultrasound imaging system and the apparatus, wherein the computing platform is configured to collect one-dimensional (1D) ultrasound scan lines through translation of the at least one ultrasound transducer through the pattern aligned over an approximation of a location of at least one organ or tissue in the small animal, and to analyze the 1D ultrasound scan lines to build a two-dimensional (2D) or three-dimensional mesh of relevant surfaces of the at least one organ or tissue, wherein the at least two motion stages are movable to allow generation of a three-dimensional (3D) volume ultrasound image of the small animal.

15. The system of claim 14, wherein the computing platform is configured to localize walls of surfaces or interfaces in the at least one organ or tissue to build the 3D mesh of the relevant surfaces of the at least one organ or tissue.

16. The system of claim 14, wherein the computing platform is configured to acquire b-mode images by translating the collected 1D ultrasound lines along a predetermined trajectory to build a 2D ultrasound image.

17. The system of claim 14, wherein the computing platform is configured to register the acquired ultrasound image to functional images of the at least one organ or tissue in the small animal from at least one functional imaging modality in order to target the at least one organ or tissue in the small animal at a same location of the at least one organ or tissue in the small animal as indicated in the functional images, via controlling the spatial position of the at least one ultrasound transducer relative to the platform.

18. The system of claim 17, wherein the platform comprises fiducial landmarks for registering the ultrasound image to the previously acquired functional images from the at least one functional imaging modality.

19. The system of claim 18, wherein the at least one functional imaging modality comprises at least one modality selected from the group consisting of: bioluminescence, fluorescence, cryoimaging, single-photon emission computerized tomography (SPECT), and positron emission tomography (PET).

20. The system of claim 14, wherein the computing platform is configured to perform passive gating on the acquired 1D ultrasound images to remove physio-induced motion.

21. The apparatus of claim 1 wherein the at least two motion stages are external to a housing of the at least one ultrasound transducer.

22. The method of claim 13 wherein the at least two motion stages are external to a housing of the at least one ultrasound transducer.

23. The system of claim 14 wherein the at least two motion stages are external to a housing of the at least one ultrasound transducer.

24. The apparatus of claim 1, wherein the acoustic coupling medium does not come into contact with the small animal.

25. The method of claim 13, wherein the acoustic coupling medium does not come into contact with the small animal.

26. The system of claim 14, wherein the acoustic coupling medium does not come into contact with the small animal.

27. The apparatus of claim 24 comprising means for controlling a temperature of the coupling medium.

28. The method of claim 25 comprising providing a mechanism for controlling a temperature of the coupling medium.

29. The system of claim 26 comprising means for controlling a temperature of the coupling medium.

30. The apparatus of claim 1 comprising at least one optical camera for obtaining images of the small animal in a modality other than ultrasound.

31. The method of claim 13 comprising using at least one optical camera for obtaining images of the small animal in a modality other than ultrasound.

32. The system of claim 14 comprising at least one optical camera for obtaining images of the small animal in a modality other than ultrasound.

* * * * *